(12) United States Patent
Reiffenrath et al.

(10) Patent No.: US 9,512,102 B2
(45) Date of Patent: Dec. 6, 2016

(54) 4,6-DIFLUORODIBENZOTHIOPHENE DERIVATIVES

(71) Applicant: MERCK PATENT GMBH, Darmstadt (DE)

(72) Inventors: Volker Reiffenrath, Rossdorf (DE); Harald Hirschmann, Darmstadt (DE)

(73) Assignee: MERCK PATENT GMBH, Darmstadt (DE)

( * ) Notice: Subject to any disclaimer, the term of this patent is extended or adjusted under 35 U.S.C. 154(b) by 0 days.

(21) Appl. No.: 14/693,269

(22) Filed: Apr. 22, 2015

(65) Prior Publication Data

US 2015/0299161 A1 Oct. 22, 2015

(30) Foreign Application Priority Data

Apr. 22, 2014 (DE) .................. 10 2014 005 713

(51) Int. Cl.
| | | |
|---|---|---|
| *G02F 1/1333* | (2006.01) | |
| *C07D 333/76* | (2006.01) | |
| *C07D 409/04* | (2006.01) | |
| *C09K 19/34* | (2006.01) | |

(52) U.S. Cl.
CPC .......... *C07D 333/76* (2013.01); *C07D 409/04* (2013.01); *C09K 19/3491* (2013.01)

(58) Field of Classification Search
CPC ............. C07D 333/76; C07D 409/04; C09K 19/3491
USPC ............. 252/299.01, 299.6, 299.61; 428/1.1
See application file for complete search history.

(56) References Cited

U.S. PATENT DOCUMENTS

| | | | | |
|---|---|---|---|---|
| 7,018,685 B2 * | 3/2006 | Schmidt | .................. | C07C 25/22 252/299.61 |
| 7,371,437 B2 * | 5/2008 | Klasen-Memmer | | C09K 19/3405 252/299.01 |
| 7,514,127 B2 * | 4/2009 | Lietzau | .................. | C07C 25/22 252/299.61 |

FOREIGN PATENT DOCUMENTS

| | | |
|---|---|---|
| DE | 102005012585 A1 | 11/2005 |
| WO | 02055463 A1 | 7/2002 |

OTHER PUBLICATIONS

European Search Report for related European Patent Application No. 15000926 dated Aug. 13, 2015.
English Abstract of WO02055463, Publication Date: Jul. 18, 2002.
English Abstract of DE102005012585, Publication Date: Nov. 3, 2005.

* cited by examiner

*Primary Examiner* — Geraldina Visconti
(74) *Attorney, Agent, or Firm* — Millen White Zelano and Branigan, PC; Csaba Henter; Anthony Zelano

(57) ABSTRACT

4,6-difluorodibenzothiophene compounds of formula I

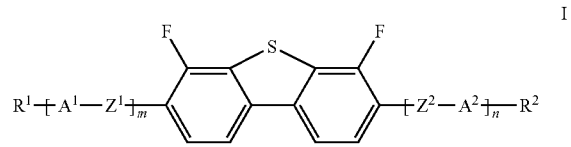

the preparation thereof, the use thereof as components in liquid-crystalline media and electro-optical display elements which contain the liquid-crystalline media.

20 Claims, No Drawings

4,6-DIFLUORODIBENZOTHIOPHENE DERIVATIVES

The present invention relates to 4,6-difluorodibenzothiophene derivatives, to a process for the preparation thereof, to liquid-crystalline media comprising these derivatives, and to electro-optical display elements containing these liquid-crystalline media. The compounds have negative dielectric anisotropy.

Liquid crystals have found widespread use since the first commercially usable liquid-crystalline compounds were found about 30 years ago. Known areas of application of conventional mixtures are, in particular, displays for watches and pocket calculators, and large display panels as used in railway stations, airports and sports arenas. Further areas of application are displays of portable and desktop computers, navigation systems and video applications. For the last-mentioned applications in particular, high demands are made of the response times and contrast of the images.

The spatial arrangement of the molecules in a liquid crystal has the effect that many of its properties are direction-dependent. Of particular importance for use in liquid-crystal displays are the optical, dielectric and elastomechanical anisotropies. Depending on whether the molecules are oriented with their longitudinal axes perpendicular or parallel to the two plates of a capacitor, the latter has a different capacitance; in other words, the dielectric constant $\in$ of the liquid-crystalline medium has different values for the two orientations. Substances whose dielectric constant is larger when the longitudinal axes of the molecules are oriented perpendicular to the capacitor plates than when they are oriented parallel are referred to as dielectrically positive. In other words, if the dielectric constant $\in_{\parallel}$ parallel to the longitudinal axes of the molecules is larger than the dielectric constant $\in_{\perp}$ perpendicular to the longitudinal axes of the molecules, the dielectric anisotropy $\Delta\in = \in_{\parallel} - \in_{\perp}$ is greater than zero. Most liquid crystals used in conventional displays fall into this group.

Both the polarisability of the molecule and the permanent dipole moment play a role for the dielectric anisotropy. On application of a voltage to the display, the longitudinal axis of the molecules orients itself in such a way that the larger of the dielectric constants becomes effective. The strength of the interaction with the electric field depends on the difference between the two constants.

In the case of the liquid-crystalline molecules used in conventional liquid-crystal displays, the dipole moment oriented along the longitudinal axis of the molecules is greater than the dipole moment oriented perpendicular to the longitudinal axis of the molecules.

By means of liquid crystals in which the greater dipole moment is oriented parallel to the longitudinal axis of the molecule, very high-performance displays have already been developed. In most cases here, mixtures of from 5 to 20 components are used in order to achieve a sufficiently broad temperature range of the mesophase and short response times and low threshold voltages. However, difficulties are still caused by the strong viewing angle dependence in liquid-crystal displays as are used, for example, for laptops. The best imaging quality can be achieved if the surface of the display is perpendicular to the viewing direction of the observer. If the display is tilted relative to the observation direction, the imaging quality deteriorates drastically under certain circumstances. For greater comfort, attempts are being made to maximise the angle through which the display can be tilted from the viewing direction of an observer without significantly reducing the imaging quality. Attempts have recently been made to improve the viewing-angle dependence using liquid-crystalline compounds whose dipole moment perpendicular to the longitudinal axis of the molecule is larger than that parallel to the longitudinal axis of the molecule. The dielectric anisotropy $\Delta\in$ is negative in this case. In the field-free state, these molecules are oriented with their longitudinal axis perpendicular to the glass surface of the display. Application of an electric field causes them to orient themselves more or less parallel to the glass surfaces. In this way, it has been possible to achieve an improvement in the viewing-angle dependence. Displays of this type are known as VA-TFT ("vertically aligned") displays.

Development in the area of liquid-crystalline materials is still far from complete. In order to improve the properties of liquid-crystalline display elements, attempts are constantly being made to develop novel compounds which enable optimisation of such displays.

The specifications WO 02/055463, DE 102005012585 and EP 1752510 disclose dibenzothiophene derivatives for use as liquid-crystalline material. The compounds differ from the compounds according to the invention in the substitution of the dibenzothiophene structure. The specifications do not disclose any physical data on comparable compounds.

It is an object of the present invention to provide compounds having advantageous properties for use in liquid-crystalline media. In particular, they should have negative dielectric anisotropy, which makes them particularly suitable for use in liquid-crystalline media for VA displays. Irrespective of the dielectric anisotropy corresponding to the display type, compounds are desired which have a favourable combination of the applicational parameters. Of these parameters, which are to be optimised simultaneously, particular mention should be made of a high clearing point, a low rotational viscosity, an optical anisotropy in the use range, and the properties which serve to achieve mixtures having the desired liquid-crystalline phases over a broad temperature range (lower melting point, good miscibility with other liquid-crystalline components of the desired type).

This object is achieved in accordance with the invention by compounds of the general formula I

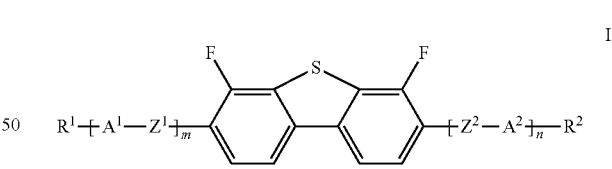

in which
m and n, independently of one another, are 0, 1 or 2, preferably 0,
$R^1$ and $R^2$, independently of one another, denote an alkyl or alkoxy radical having 1 to 15 C atoms, where, in addition, one or more $CH_2$ groups in these radicals may each be replaced, independently of one another, by —C≡C—, —$CF_2$O—, —$OCF_2$—, —CH=CH—,

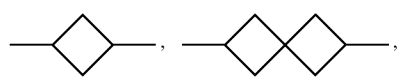

—O—, —CO—O— or —O—CO— in such a way that O atoms are not linked directly to one another, and in which, in addition, one or more H atoms may be replaced by halogen,
preferably, independently of one another, an unsubstituted alkyl radical or alkoxy radical having 1 to 15 carbon atoms or an alkenyl, alkenyloxy or alkynyl radical having 2 to 15 C atoms, which are in each case optionally mono- or polyhalogenated, $A^1$ and $A^2$, independently of one another, denote a radical selected from the following groups:
a) 1,4-phenylene, in which, in addition, one or two CH groups may be replaced by N and in which, in addition, one or more H atoms may be replaced by a group L,
b) the group consisting of trans-1,4-cyclohexylene and 1,4-cyclohexenylene, in which, in addition, one or more non-adjacent $CH_2$ groups may be replaced by —O— and/or —S— and in which, in addition, one or more H atoms may be replaced by F or Cl, and
c) the group consisting of tetrahydropyran-2,5-diyl, 1,3-dioxane-2,5-diyl, tetrahydrofuran-2,5-diyl, cyclobutane-1,3-diyl, piperidine-1,4-diyl, thiophene-2,5-diyl and selenophene-2,5-diyl, each of which may also be mono- or polysubstituted by a group L, L on each occurrence, independently, denotes F, Cl, CN, $SCN$, $SF_5$ or straight-chain or branched, in each case optionally fluorinated, alkyl, alkoxy, alkylcarbonyl, alkoxycarbonyl, alkylcarbonyloxy or alkoxycarbonyloxy having 1 to 12 or preferably 1 to 4 C atoms, and $Z^1$ and $Z^2$, independently of one another, denote a single bond, —$CF_2O$—, —$OCF_2$—, —$CH_2O$—, —$OCH_2$—, —(CO)O—, —(CO)—, —$(CH_2)_4$—, —$CH_2CH_2$—, —$CF_2$—$CF_2$—, —$CF_2$—$CH_2$—, —$CH_2$—$CF_2$—, —CH=CH—, —CF=CF—, —CF=CH—, —CH=CF—, —$(CH_2)_3O$—, —$O(CH_2)_3$—, —C≡C—, —O—, —$CH_2$—, —$(CH_2)_3$— or —$CF_2$—.

The compounds have a clearly negative $\Delta\varepsilon$ and are therefore suitable, in particular, for use in liquid-crystal mixtures for VA-TFT displays. The compounds according to the invention preferably have a $\Delta\varepsilon \leq -4$, more preferably $\Delta\varepsilon \leq -6$ and particularly preferably a $\Delta\varepsilon \leq -8$. They exhibit good miscibility with the conventional substances used in liquid-crystal mixtures for displays, i.e. they have good solubility therein. The rotational viscosities of the compounds and of the resultant liquid-crystalline mixtures are advantageously low.

The other physical, physicochemical or electro-optical parameters of the compounds according to the invention are also advantageous for use of the compounds in liquid-crystalline media. The liquid-crystalline media which comprise these compounds have, in particular, an adequate width of the nematic phase and good low-temperature and long-term stability as well as sufficiently high clearing points. The low melting points of the compounds according to the invention give an indication of the advantageous mixing behaviour. Furthermore, the compounds of the formula I according to the invention have values of the optical anisotropy $\Delta n$ which are suitable, in particular, for use in VA-TFT displays. The compounds according to the invention preferably have a $\Delta n$ of greater than 0.15 and less than 0.25. In addition, the compounds are relatively simple to prepare. The balanced combination of these advantageous properties represents a significant enrichment of the mixture components which are available for VA mixtures.

The parameters m and n in the sum m+n preferably have a value of 0 or 1, particularly 0. m is thus preferably 0 or 1, preferably 0, and n is preferably 0.

$R^1$ and $R^2$ preferably each, independently of one another, denote an alkoxy radical, alkyl radical or alkenyl radical having 1 to 7 or 2 to 7 carbon atoms respectively. $R^1$ and $R^2$ in the general formula I are particularly preferably, independently of one another, an alkoxy radical or alkyl radical having 2 to 7 C atoms. The radicals $R^1$ and $R^2$ are preferably different here.

In the case where m=0, $R^1$ preferably denotes an alkoxy, alkyl or alkenyl group, particularly preferably an alkoxy group having 1-7 C atoms, particularly preferably having 2 to 5 C atoms. In the case where n=0, $R^2$ preferably denotes an alkoxy, alkyl or alkenyl group, particularly preferably an alkoxy group having 1-7 C atoms, particularly preferably having 2 to 7 C atoms. The sum of the number of carbon atoms in $R^1$ and $R^2$ together is preferably 4, 5, 6, 7, 8, 9 or 10, particularly preferably 6, 7, 8, 9 or 10.

In the case where m=1 or 2, $R^1$ preferably denotes an alkyl, alkoxy or alkenyl group, particularly preferably an alkyl group having 1-7 C atoms, particularly preferably having 2 to 5 C atoms. In the case where n=1 or 2, $R^2$ preferably denotes an alkyl or alkenyl group, particularly preferably an alkyl group having 1-7 C atoms, particularly preferably having 2 to 5 C atoms.

If $R^1$ and $R^2$ in formula I each, independently of one another, represent an alkyl radical, these are straight-chain or branched. Each of these radicals is preferably straight-chain, has, unless indicated otherwise, 1, 2, 3, 4, 5, 6 or 7 C atoms and is accordingly preferably methyl, ethyl, propyl, butyl, pentyl, hexyl or heptyl.

$R^1$ and $R^2$ in the formula I may furthermore each, independently of one another, be an alkenyl radical having 2 to 15 C atoms which is straight-chain or branched and has at least one C=C double bond. It is preferably straight-chain and has 2 to 7 C atoms. Accordingly, it is preferably vinyl, prop-1- or -2-enyl, but-1-, -2- or -3-enyl, pent-1-, -2-, -3- or -4-enyl, hex-1-, -2-, -3-, -4- or -5-enyl, or hept-1-, -2-, -3-, -4-, -5- or -6-enyl. If the two C atoms of the C=C double bond are substituted, the alkenyl radical can be in the form of the E and/or Z isomer (trans/cis). In general, the respective E isomers are preferred. Of the alkenyl radicals, particular preference is given to prop-2-enyl, but-2- or -3-enyl, and pent-3- or -4-enyl.

$R^1$ and $R^2$ in the formula I may, independently of one another, also be an alkynyl radical having 2 to 15 C atoms which is straight-chain or branched and has at least one C≡C triple bond. Preference is given to 1- or 2-propynyl and 1-, 2- or 3-propynyl.

The groups $A^1$ and $A^2$ preferably denote, independently, a disubstituted cyclic group selected from the formulae

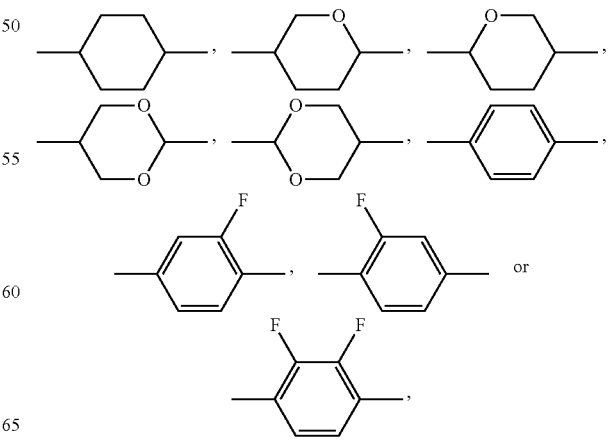

in particular

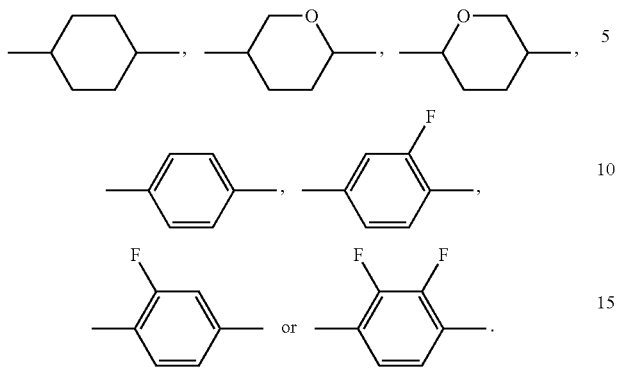

The group $Z^1$ preferably denotes a single bond, —CH$_2$O—, —CF$_2$O— or —OCF$_2$—, particularly preferably a single bond.

The group $Z^2$ preferably denotes a single bond, —OCH$_2$—, —OCF$_2$— or —CF$_2$O—, particularly preferably a single bond.

The group L preferably denotes F, Cl, —CF$_3$ or an alkyl or alkoxy group having 1, 2 or 3 carbon atoms.

Particularly preferably, m and n denote 0 and $R^1$ and $R^2$ each denote an alkoxy group having 1 to 7 carbon atoms.

Halogen in connection with the present invention denotes fluorine, chlorine, bromine or iodine, in particular fluorine or chlorine.

In connection with the present invention, the term "alkyl"—unless defined otherwise elsewhere in this description or in the claims—denotes a straight-chain or branched, saturated, aliphatic hydrocarbon radical having 1 to 15 (i.e. 1, 2, 3, 4, 5, 6, 7, 8, 9, 10, 11, 12, 13, 14 or 15) carbon atoms.

Particular preference is given to compounds of the formula I according to the invention selected from the sub-formulae IA to IC:

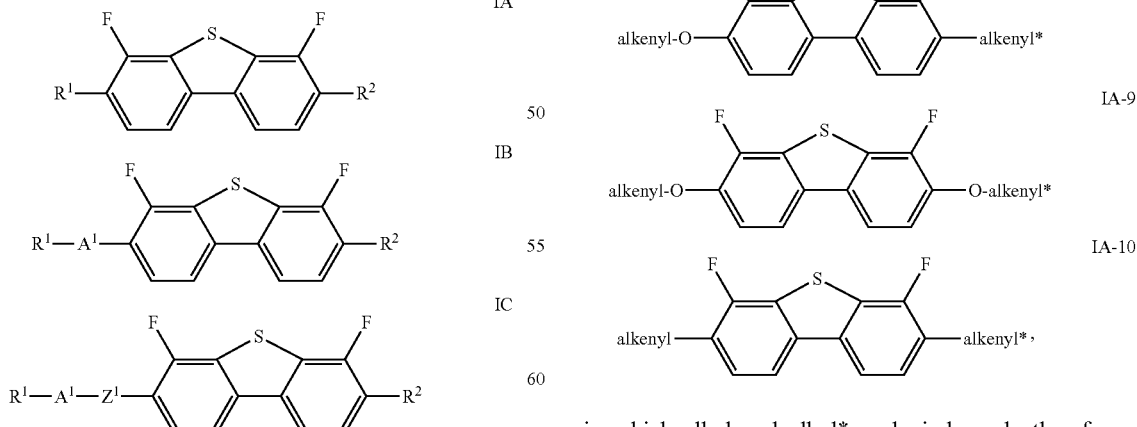

in which $R^1$, $R^2$ and $A^1$ have the meanings as defined above for the formula I, and $Z^1$ is a group as defined above without the single bond.

Preferred compounds of the formula IA are the compounds of the formulae IA-1 to IA-10,

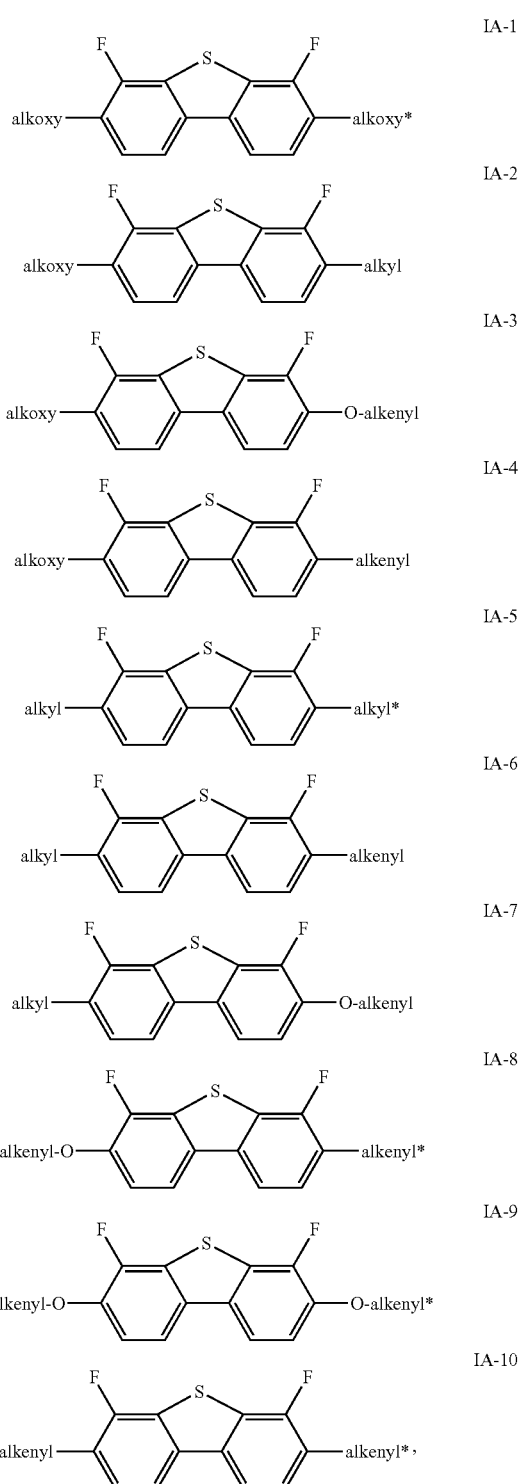

in which alkyl and alkyl* each, independently of one another, denote a straight-chain alkyl radical having 1-7 C atoms, alkenyl and alkenyl* each, independently of one another, denote a straight-chain alkenyl radical having 2-7 C atoms, alkoxy and alkoxy* each, independently of one another, denote a straight-chain alkoxy radical having 1-7 C atoms. Particular preference is given to the compounds of the formulae IA-1, IA-2, IA-3, IA-4, IA-7 and IA-9.
Preferred compounds of the formulae IB and IC are the compounds of the formulae
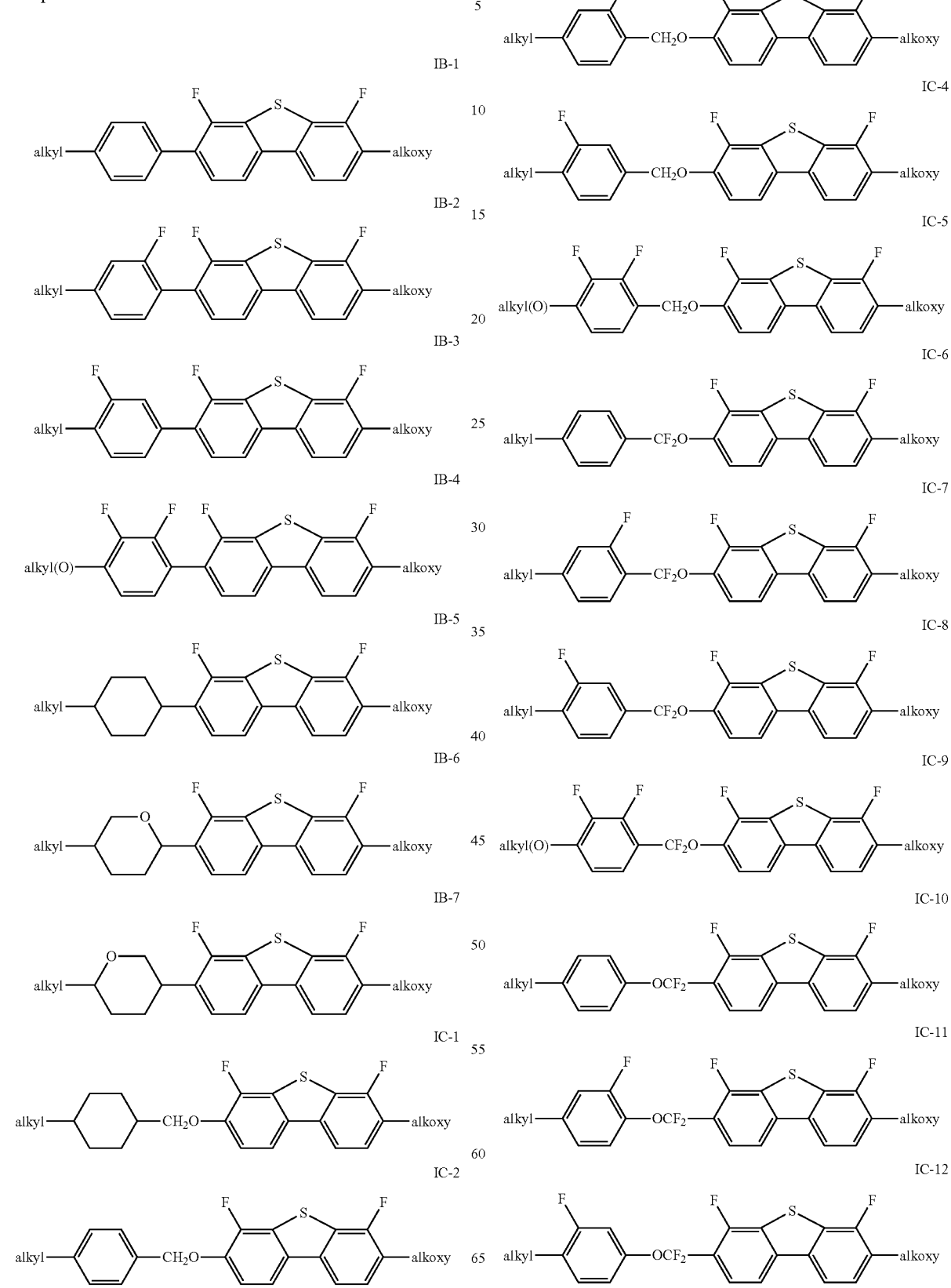

-continued

IC-13
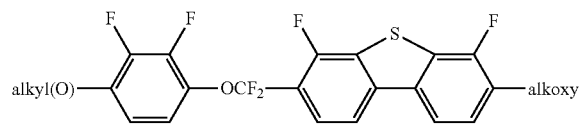

in which alkyl, independently of one another, denotes a straight-chain alkyl radical having 1-7 C atoms. The radical alkyl(O) stands for alkyl or alkoxy having 1 to 7 C atoms. Of these, particular preference is given to the compounds of the formulae IB-5 to IC-13.

Preferred compounds of the formula IA-1 are selected from those of the formulae IA-1-1 to IA-1-25:

IA-1-1
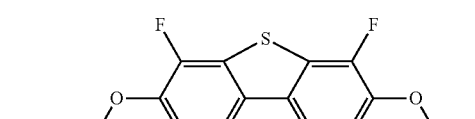

IA-1-2
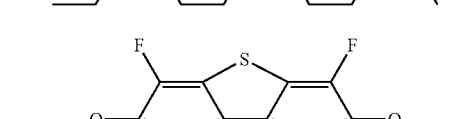

IA-1-4
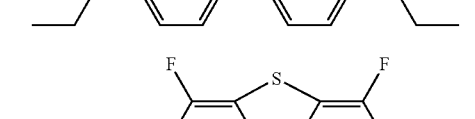

IA-1-5
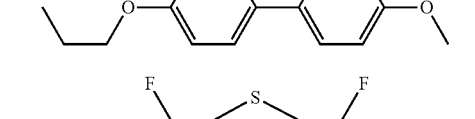

IA-1-6
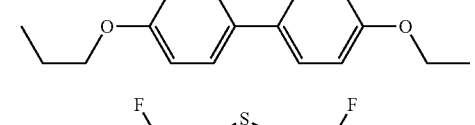

IA-1-7
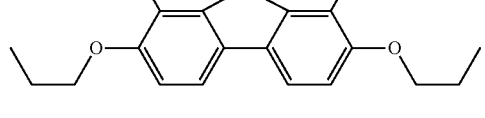

IA-1-8
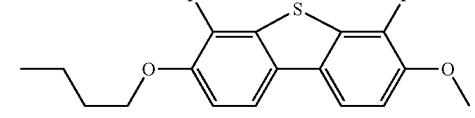

IA-1-9
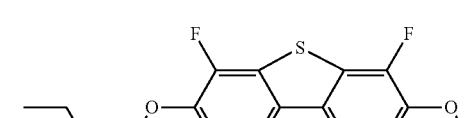

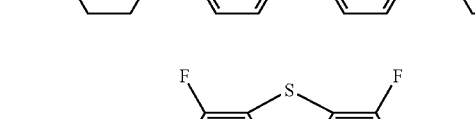
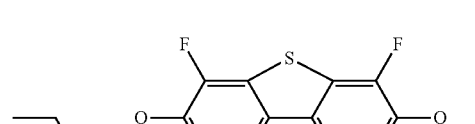

-continued

IA-1-10
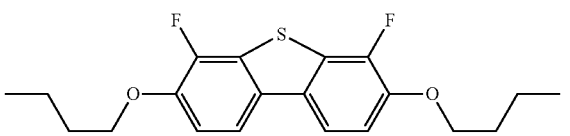

IA-1-11
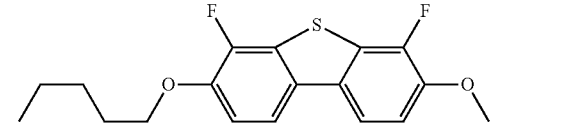

IA-1-12
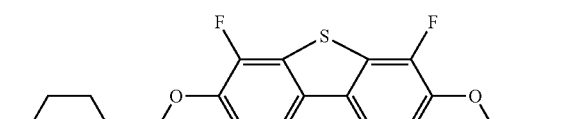

IA-1-13
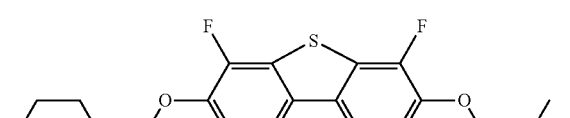

IA-1-14
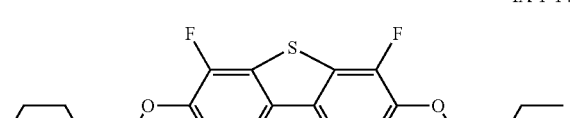

IA-1-15
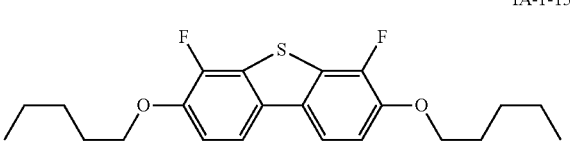

IA-1-16
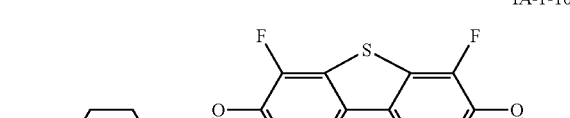

IA-1-17
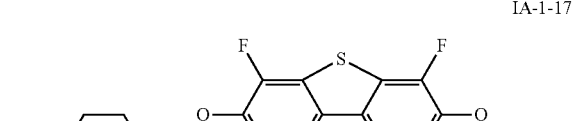

IA-1-18
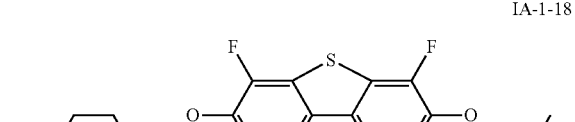

IA-1-19
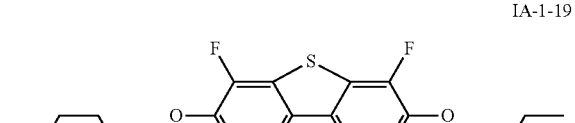

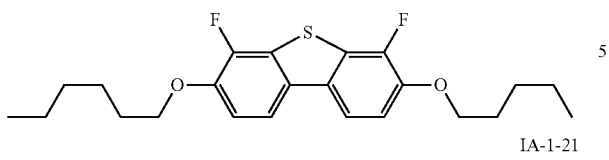
IA-1-20
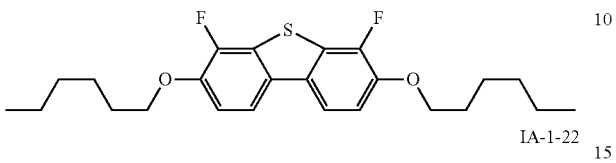
IA-1-21
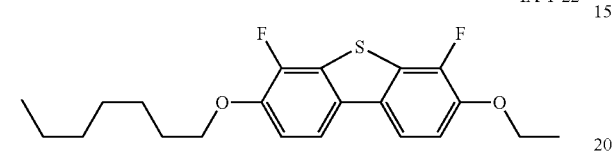
IA-1-22
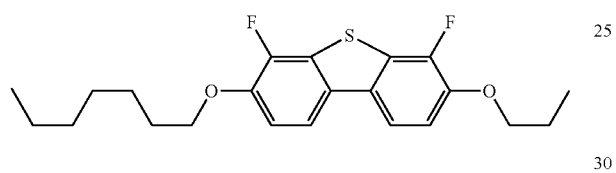
IA-1-23
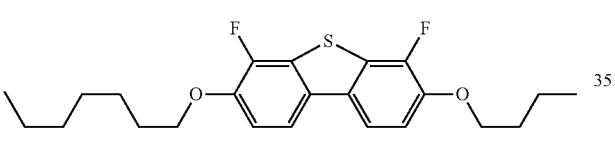
IA-1-24
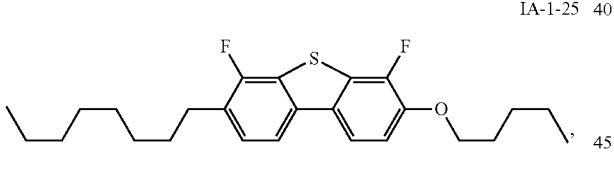
IA-1-25
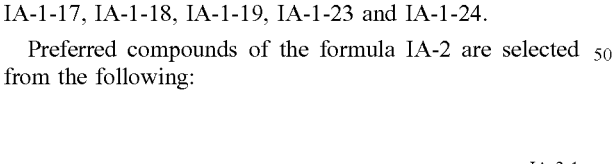
in particular of the formulae IA-1-8, IA-1-12, IA-1-13, IA-1-17, IA-1-18, IA-1-19, IA-1-23 and IA-1-24.
Preferred compounds of the formula IA-2 are selected from the following:
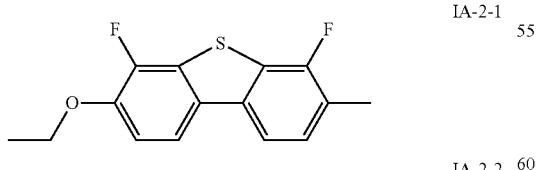
IA-2-1
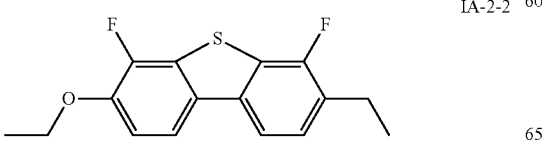
IA-2-2
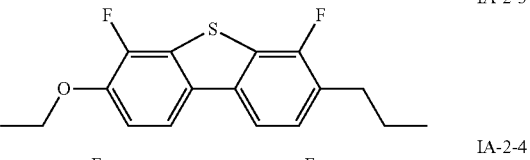
IA-2-3
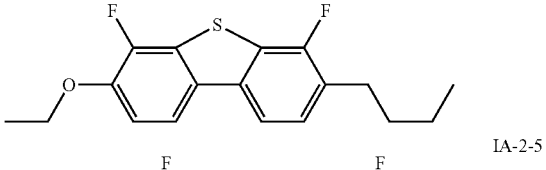
IA-2-4
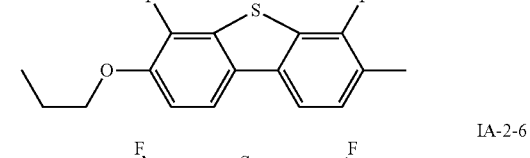
IA-2-5
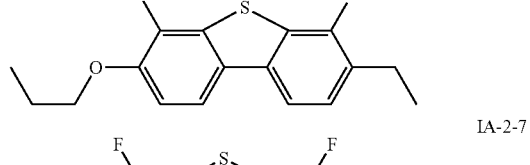
IA-2-6
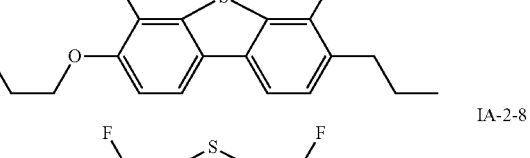
IA-2-7
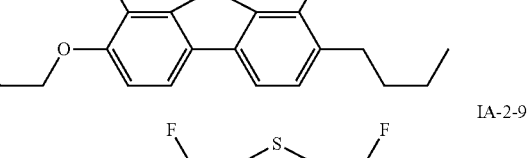
IA-2-8
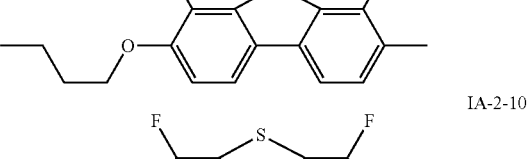
IA-2-9
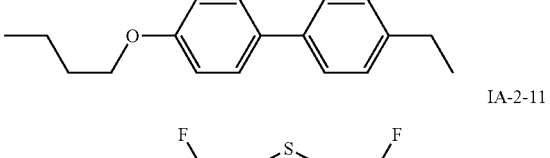
IA-2-10
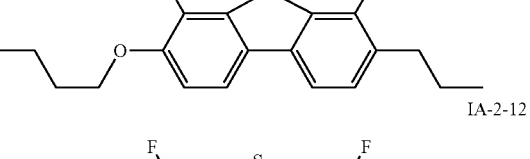
IA-2-11
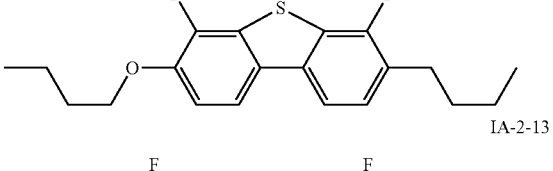
IA-2-12
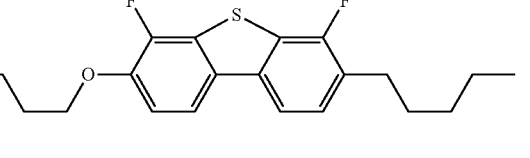
IA-2-13

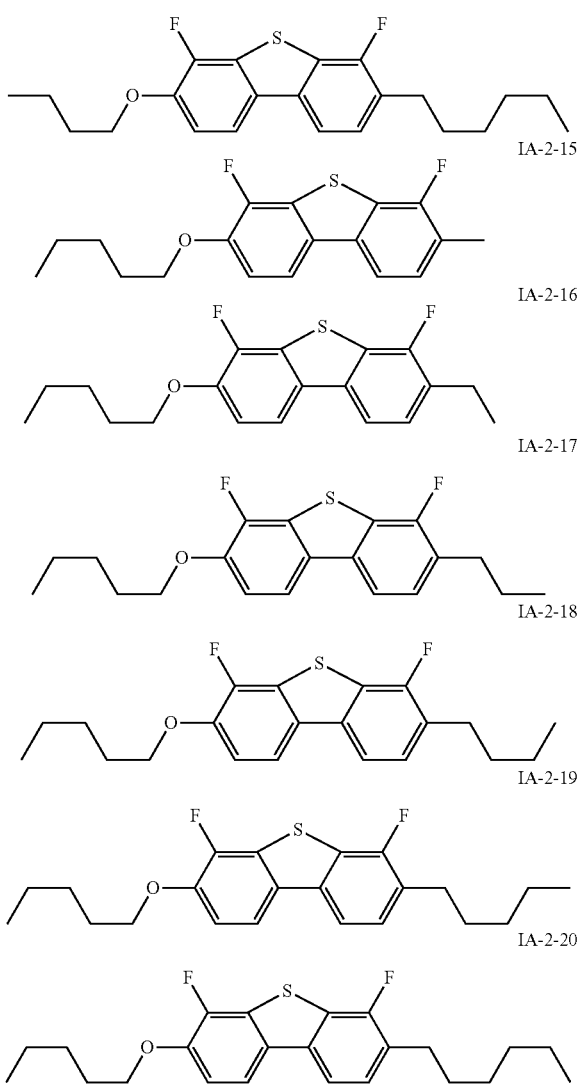

IA-2-14
IA-2-15
IA-2-16
IA-2-17
IA-2-18
IA-2-19
IA-2-20

Of these, particular preference is given to the compounds of the formulae IA-2-7, IA-2-8, IA-2-12, IA-2-13, IA-2-16, IA-2-17 and IA-2-18.

If radicals or substituents of the compounds according to the invention or the compounds according to the invention themselves are in the form of optically active or stereoisomeric radicals, substituents or compounds since they have, for example, a centre of asymmetry, these are likewise encompassed by the present invention. It goes without saying here that the compounds of the general formula I according to the invention may exist in isomerically pure form, for example as pure enantiomers, diastereomers, E or Z isomers, trans or cis isomers, or as a mixture of a plurality of isomers in any desired ratio, for example as a racemate, E/Z isomer mixture or as a cis/trans isomer mixture.

The 1,4-substituted cyclohexyl ring of the formula

or -Cycin the compounds disclosed for liquid-crystalline media preferably has the trans configuration, i.e. the two substituents are both in the equatorial position in the thermodynamically preferred chair conformation.

The compounds of the general formula I can be prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can be made here of variants known per se which are not mentioned here in greater detail.

If desired, the starting materials can also be formed in situ by not isolating them from the reaction mixture, but instead immediately converting them further into the compounds of the general formula I.

The syntheses of compounds of the general formula I according to the invention are described by way of example in the examples. The starting substances can be obtained by generally accessible literature procedures or are commercially available.

Particularly suitable synthetic routes to the compounds according to the invention are explained below with reference to Schemes 1 to 6.

The substituents $R^1$, $R^2$ and the indices m and n in the following schemes have the meanings as indicated for the formula I.

The synthesis of the compounds of the formula I containing two alkoxy groups ($R^1$, $R^2$) and m/n=0 is carried out starting from the basic compound dibenzothiophene (cf. Scheme 1).

Scheme 1. Synthesis of the compounds of the formula I.

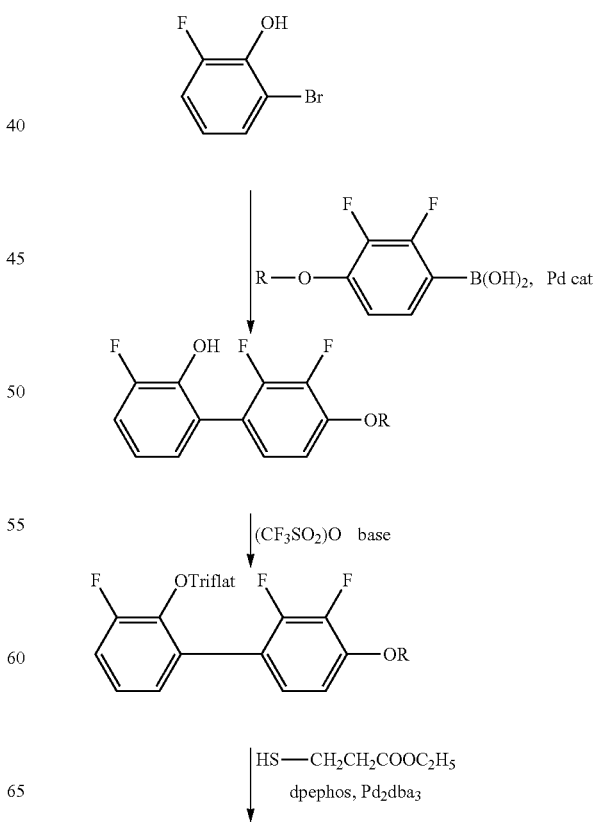

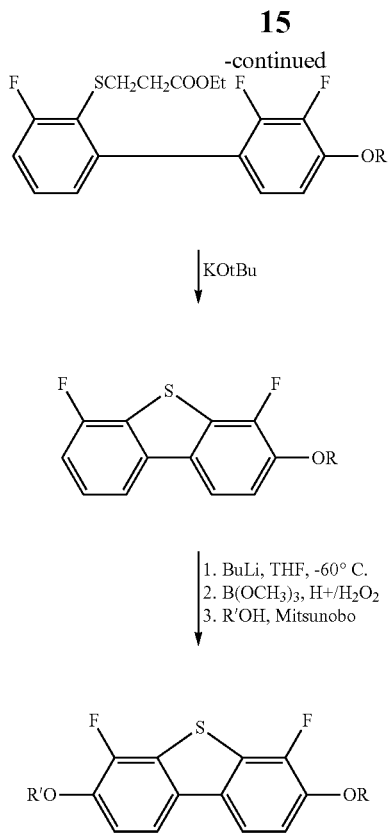

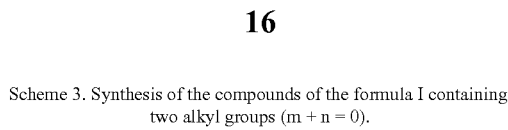

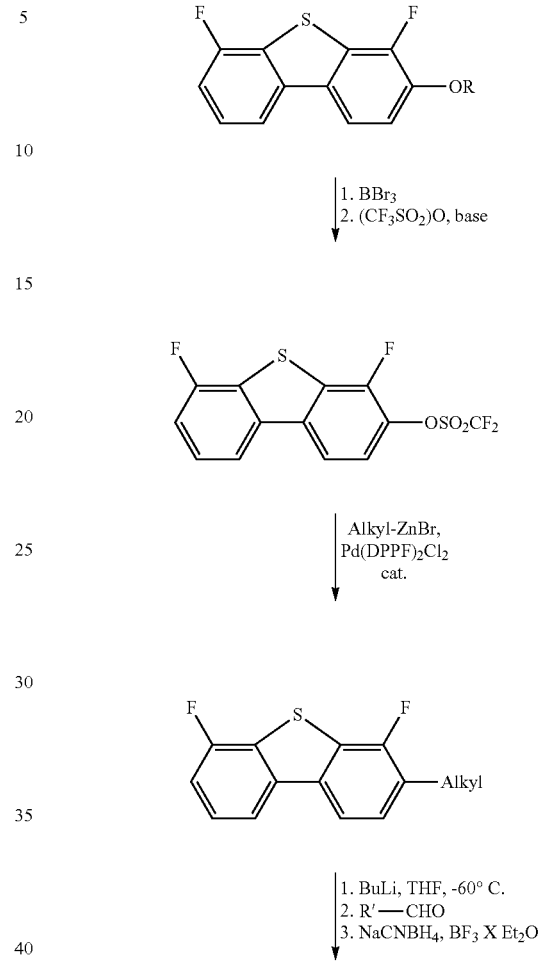

The radicals —R, —R' each, independently of one another, denote straight-chain or branched alkyl or alkenyl analogously to formula I. The Mitsunobu protocol uses the conventional reagents PPh$_3$ and ROOC—N=N—COOR, alternatively also R—Br with K$_2$CO$_3$.

The compounds containing an alkoxy group and an alkyl group (m+n=0) are prepared in a modification of the above synthesis in accordance with Scheme 2.

Scheme 2. Synthesis of the compounds of the formula I containing an alkyl and an alkoxy group (m + n = 0).

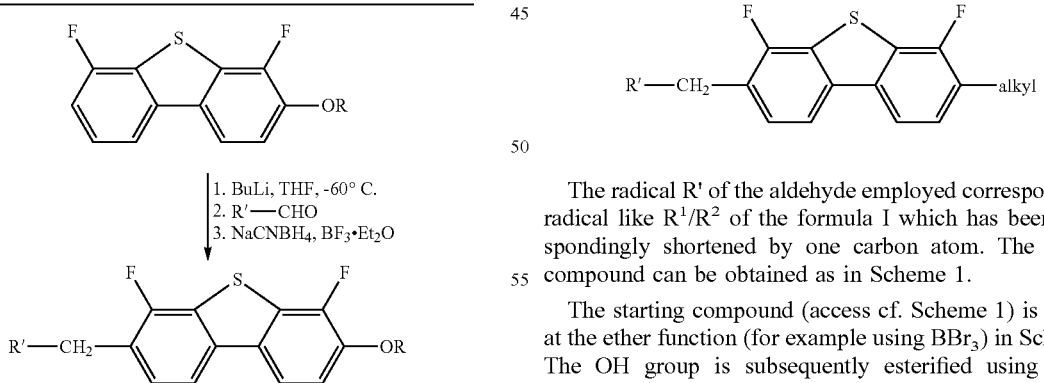

The radical R' corresponds to a radical like R$^1$/R$^2$ in formula I which has been correspondingly shortened by one carbon atom. Radical R see Scheme 1.

The synthesis of the compounds of the formula I containing two alkyl groups (m+n=0) is carried out in a further modification of the above syntheses (Scheme 3).

The radical R' of the aldehyde employed corresponds to a radical like R$^1$/R$^2$ of the formula I which has been correspondingly shortened by one carbon atom. The starting compound can be obtained as in Scheme 1.

The starting compound (access cf. Scheme 1) is cleaved at the ether function (for example using BBr$_3$) in Scheme 3. The OH group is subsequently esterified using trifluoromethanesulfonic acid and subsequently subjected to a Pd-catalysed coupling reaction with an organic zinc-halogen compound (here R$^1$—ZnBr). The further steps for the formation of the second alkyl group correspond to those from Scheme 2.

The compounds of the formula I in which further rings A$^{1/2}$ are included (m+n=1, 2) are prepared, for example, in accordance with Schemes 4 to 6:

Scheme 4. Synthesis of compounds of the formula I in which m = 1 and $Z^1$ is a single bond. Radicals R and R' cf. Scheme 2, $R^2$ also —$CH_2A^2$—$R^2$.
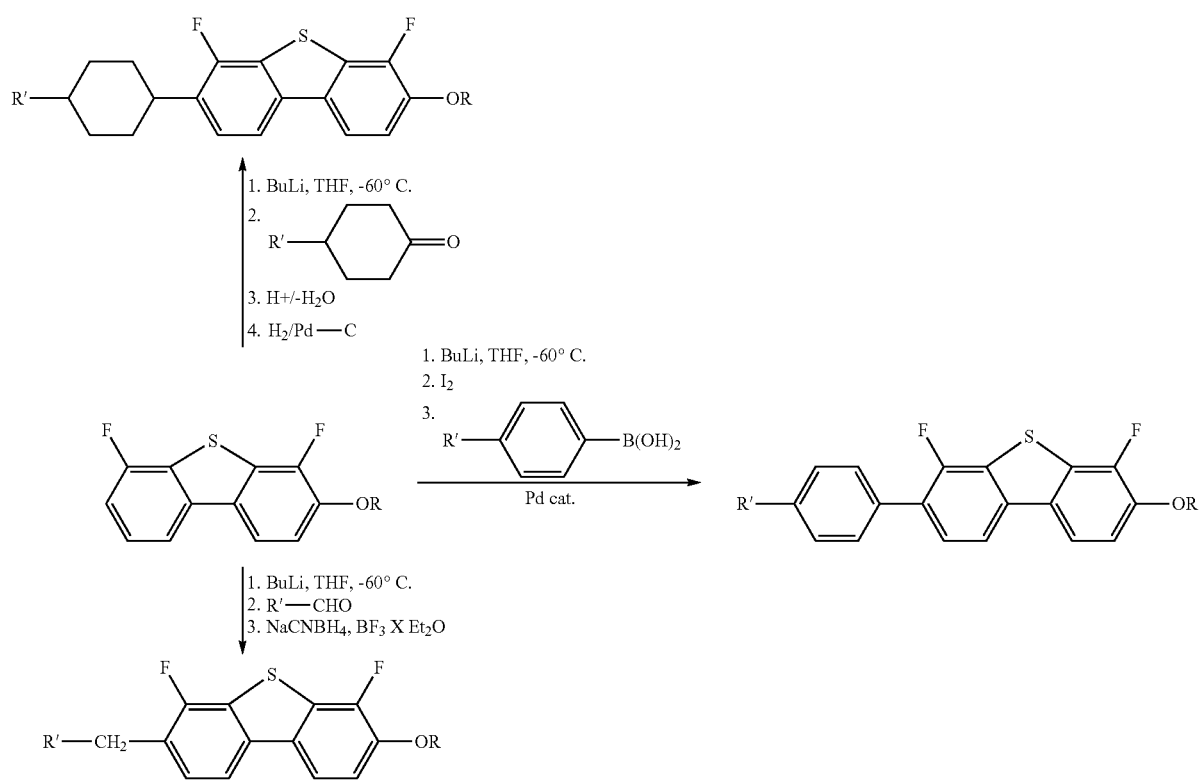
Scheme 5. Synthesis of compounds of the formula I in which m = 1, $A^1$ = tetrahydropyran and $Z^1$ is a single bond. Radicals R and R' see Scheme 1.
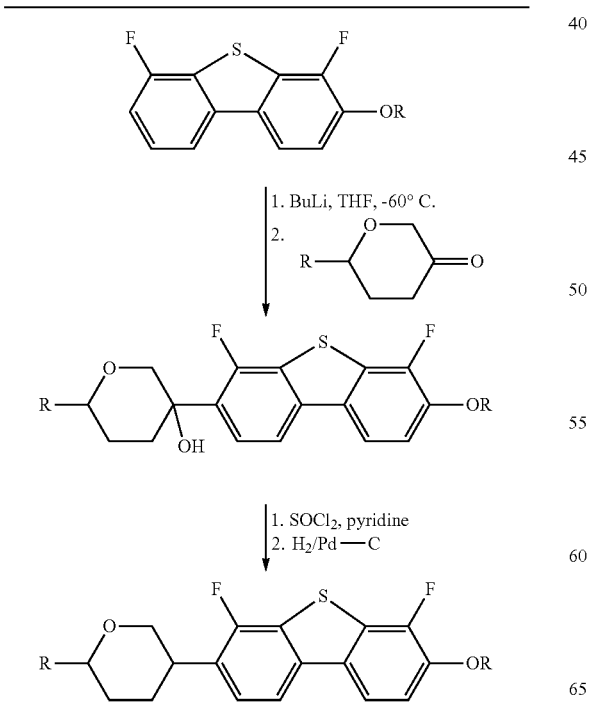

Scheme 6. Synthesis of the compounds of the formula I in which m = 1 and Z¹ = —OCF$_2$— or —CF$_2$O—. Radicals R and R' see Scheme 1.

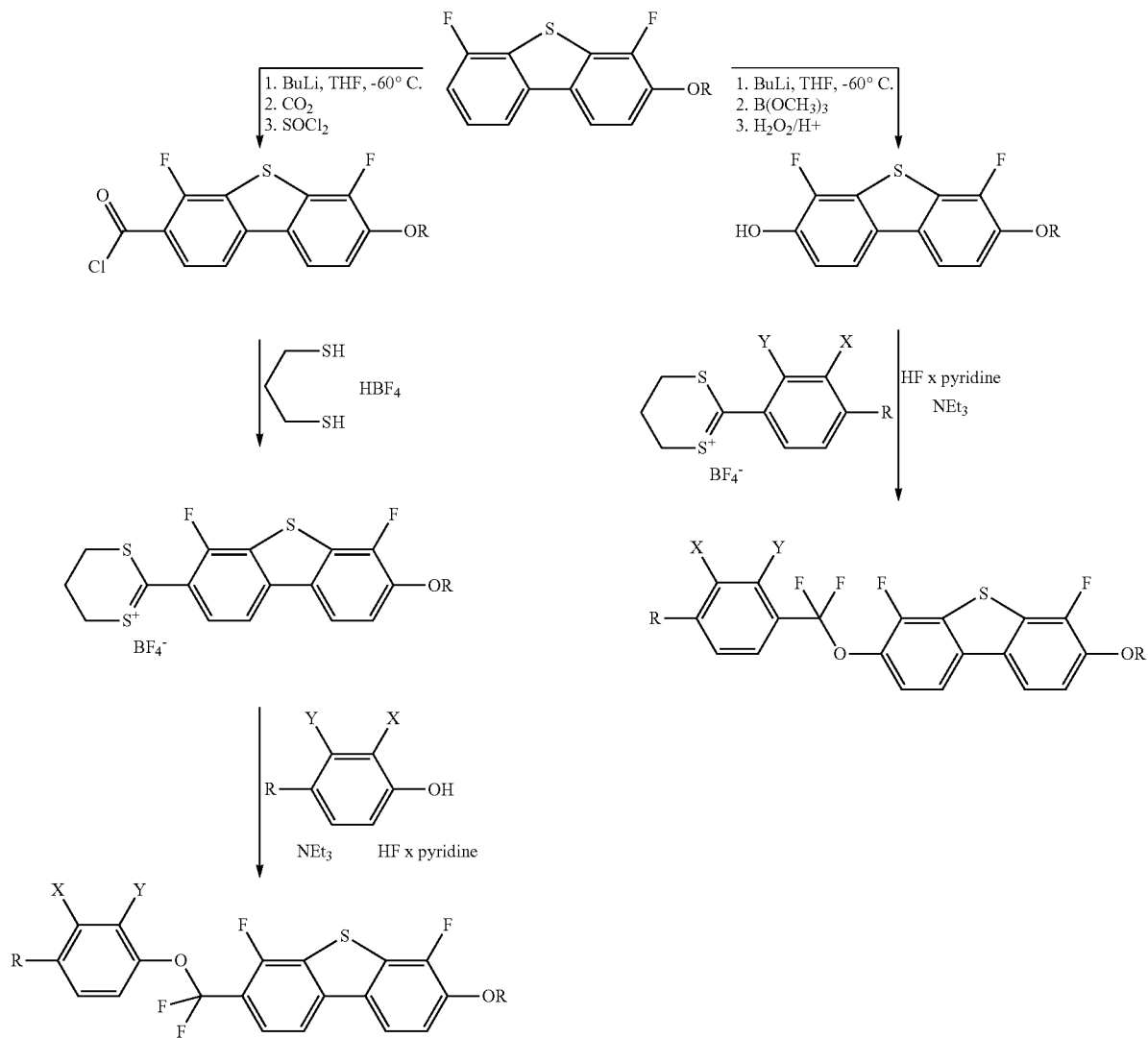

In principle, the syntheses of alkoxy radicals (here —OR) can be applied analogously to other ether compounds, for example —OCH$_2$A$^1$-R$^1$ or —OCH$_2$A$^2$-R$^2$.

The reaction schemes shown should only be regarded as illustrative. Instead of the radicals —OR and —OR' in the schemes, it is optionally also possible to introduce general radicals of the formulae R$^1$-[A$^1$-Z$^1$]$_m$— and —[Z$^2$-A$^2$]$_n$-R$^2$ analogously to the general formula I. The person skilled in the art will be able to carry out corresponding variations of the syntheses presented, and also follow other suitable synthetic routes in order to obtain compounds of the formula I.

In accordance with the syntheses depicted above, the present invention in an embodiment also encompasses one or more processes for the preparation of compounds of the formula I.

The invention thus encompasses a process for the preparation of compounds of the formula I which is characterised in that it includes a process step in which a compound of the formula (B)

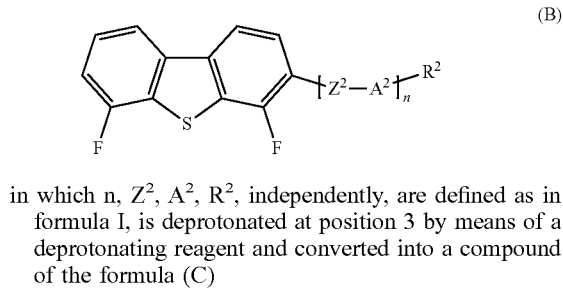

in which n, Z$^2$, A$^2$, R$^2$, independently, are defined as in formula I, is deprotonated at position 3 by means of a deprotonating reagent and converted into a compound of the formula (C)

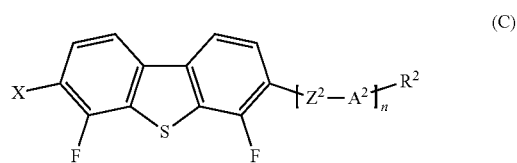

in which, independently,

X denotes B(OR)$_2$, —C(OH)R$_2$, —(CO)OH, —(CO)Cl, OH or

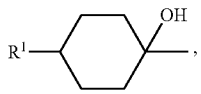

R in each case, independently, denotes H or an alkyl radical having 1 to 14 C atoms, and Z$^2$, A$^2$, n, R$^1$, R$^2$ are defined as in formula I, and in further process steps is converted into a compound of the formula I.

The various groups X in formula (C) are obtained by reacting the aromatic compound metallated in the ortho-position to the fluorine atom with trialkyl borate B(OR)$_3$ to give X=—B(OR)$_2$, with aldehyde RCHO to give —C(OH)R, 4-(R$^1$)-substituted cyclohexanones to give the corresponding alcohols and optionally converting the boronic acid group X=—B(OR)$_2$ formed into OH under oxidative conditions (for example using H$_2$O$_2$). Preferred conditions for the metallation are reaction with an alkyllithium compound, such as n-BuLi, in THF, at about −70° C., then addition of the electrophile.

The process and the subsequent work-up of the reaction mixture can basically be carried out as a batch reaction or in a continuous reaction procedure. The continuous reaction procedure encompasses, for example, reaction in a continuous stirred-tank reactor, a stirred-reactor cascade, a loop or cross-flow reactor, a flow tube or in a microreactor. The reaction mixtures are optionally worked up, as necessary, by filtration via solid phases, chromatography, separation between immiscible phases (for example extraction), adsorption onto solid supports, removal of solvents and/or azeotropic mixtures by distillation, selective distillation, sublimation, crystallisation, co-crystallisation or by nanofiltration on membranes.

As already mentioned, the compounds of the general formula I can be used in liquid-crystalline media. The present invention therefore also relates to a liquid-crystalline medium comprising at least two liquid-crystalline compounds, comprising at least one compound of the general formula I.

The present invention also relates to liquid-crystalline media comprising 2 to 40, preferably 4 to 30, components as further constituents besides one or more compounds of the formula I according to the invention. These media particularly preferably comprise 7 to 25 components besides one or more compounds according to the invention. These further constituents are preferably selected from nematic or nematogenic (monotropic or isotropic) substances, in particular substances from the classes of the azoxybenzenes, benzylideneanilines, biphenyls, terphenyls, 1,3-dioxanes, 2,5-tetrahydropyrans, phenyl or cyclohexyl benzoates, phenyl or cyclohexyl esters of cyclohexanecarboxylic acid, phenyl or cyclohexyl esters of cyclohexylbenzoic acid, phenyl or cyclohexyl esters of cyclohexylcyclohexanecarboxylic acid, cyclohexylphenyl esters of benzoic acid, of cyclohexanecarboxylic acid or of cyclohexylcyclohexanecarboxylic acid, phenylcyclohexanes, cyclohexylbiphenyls, phenylcyclohexylcyclohexanes, cyclohexylcyclohexanes, cyclohexylcyclohexenes, 1,4-biscyclohexylbenzenes, 4',4'-biscyclohexylbiphenyls, phenyl- or cyclohexylpyrimidines, phenyl- or cyclohexylpyridines, phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, 1-cyclohexyl-2-(4-phenylcyclohexyl)ethanes, 1-cyclohexyl-2-biphenylethanes, 1-phenyl-2-cyclohexyl-phenylethanes, optionally halogenated stilbenes, benzyl phenyl ethers, tolans and substituted cinnamic acids. The 1,4-phenylene groups in these compounds may also be mono- or polyfluorinated.

The most important compounds suitable as further constituents of media according to the invention can be characterised by the formulae (II), (III), (IV), (V) and (VI):

 (II)

 (III)

 (IV)

 (V)

 (VI)

In the formulae (II), (III), (IV), (V) and (VI), L and E, which may be identical or different, each, independently of one another, denote a divalent radical from the group formed by -Phe-, -Cyc-, -Phe-Phe-, -Phe-Cyc-, -Cyc-Cyc-, -Pyr-, -Dio-, -Thp-, -G-Phe- and -G-Cyc- and their mirror images, where Phe denotes unsubstituted or fluorine-substituted 1,4-phenylene, Cyc denotes trans-1,4-cyclohexylene or 1,4-cyclohexenylene, Pyr denotes pyrimidine-2,5-diyl or pyridine-2,5-diyl, Dio denotes 1,3-dioxane-2,5-diyl, Thp denotes tetrahydropyran-2,5-diyl and G denotes 2-(trans-1,4-cyclohexyl)ethyl, pyrimidine-2,5-diyl, pyridine-2,5-diyl, 1,3-dioxane-2,5-diyl or tetrahydropyran-2,5-diyl.

One of the radicals L and E is preferably Cyc or Phe. E is preferably Cyc, Phe or Phe-Cyc. The media according to the invention preferably comprise one or more components selected from the compounds of the formulae (II), (III), (IV), (V) and (VI) in which L and E are selected from the group consisting of Cyc and Phe and simultaneously one or more components selected from the compounds of the formulae (II), (III), (IV), (V) and (VI) in which one of the radicals L and E is selected from the group consisting of Cyc and Phe and the other radical is selected from the group consisting of -Phe-Phe-, -Phe-Cyc-, -Cyc-Cyc-, -G-Phe- and -G-Cyc-, and optionally one or more components selected from the compounds of the formulae (II), (III), (IV), (V) and (VI) in which the radicals L and E are selected from the group consisting of -Phe-Cyc-, -Cyc-Cyc-, -G-Phe- and -G-Cyc-.

In a smaller sub-group of the compounds of the formulae (II), (III), (IV), (V) and (VI), R' and R" each, independently of one another, denote alkyl, alkenyl, alkoxy, alkoxyalkyl (oxaalkyl), alkenyloxy or alkanoyloxy having up to 8 C atoms. This smaller sub-group is called group A below, and the compounds are referred to by the sub-formulae (IIa), (IIIa), (IVa), (Va) and (VIa). In most of these compounds, R' and R" are different from one another, one of these radicals usually being alkyl, alkenyl, alkoxy or alkoxyalkyl (oxaalkyl).

In another smaller sub-group of the compounds of the formulae (II), (III), (IV), (V) and (VI), which is known as group B, E denotes

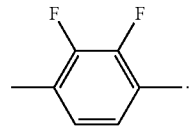

In the compounds of group B, which are referred to by the sub-formulae (IIb), (IIIb), (IVb), (Vb) and (VIb), R' and R" are as defined for the compounds of the sub-formulae (IIa) to (VIa) and are preferably alkyl, alkenyl, alkoxy or alkoxyalkyl (oxaalkyl).

In a further smaller sub-group of the compounds of the formulae (II), (III), (IV), (V) and (VI), R" denotes —CN. This sub-group is referred to below as group C, and the compounds of this sub-group are correspondingly described by sub-formulae (IIc), (IIIc), (IVc), (Vc) and (VIc). In the compounds of the sub-formulae (IIc), (IIIc), (IVc), (Vc) and (VIc), R' is as defined for the compounds of the sub-formulae (IIa) to (VIa) and is preferably alkyl, alkenyl, alkoxy or alkoxyalkyl (oxaalkyl).

Besides the preferred compounds of groups A, B and C, other compounds of the formulae (II), (III), (IV), (V) and (VI) having other variants of the proposed substituents are also customary. All these substances are obtainable by methods which are known from the literature or analogously thereto.

Besides the compounds of the general formula I according to the invention, the media according to the invention preferably comprise one or more compounds from groups A, B and/or C. The proportions by weight of the compounds from these groups in the media according to the invention are:

group A:
from 0 to 90%, preferably from 20 to 90%, in particular from 30 to 90%.
group B:
from 0 to 80%, preferably from 10 to 80%, in particular from 10 to 70%.
group C:
from 0 to 80%, preferably from 5 to 80%, in particular from 5 to 50%.

The media according to the invention preferably comprise from 1 to 40%, particularly preferably from 5 to 30%, of the compounds of the formula I according to the invention. The media preferably comprise one, two, three, four or five compounds of the formula I according to the invention.

The media according to the invention are prepared in a manner conventional per se. In general, the components are dissolved in one another, preferably at elevated temperature. By means of suitable additives, the liquid-crystalline phases of the present invention can be modified in such a way that they can be used in all types of liquid-crystal display element that have been disclosed hitherto. Additives of this type are known to the person skilled in the art and are described in detail in the literature (H. Kelker/R. Hatz, Handbook of Liquid Crystals, Verlag Chemie, Weinheim, 1980). For example, pleochroic dyes can be added for the production of coloured guest-host systems or substances can be added in order to modify the dielectric anisotropy, the viscosity and/or the alignment of the nematic phases.

Owing to their negative $\Delta\varepsilon$, the compounds of the formula I are particularly suitable for use in VA-TFT displays.

The present invention therefore also relates to electro-optical display elements containing a liquid-crystalline medium according to the invention. The display element is preferably a VA-TFT display element (VA: vertical alignment; TFT: thin-film transistor).

Further combinations of the embodiments and variants of the invention in accordance with the description arise from the claims.

Further embodiments of the present invention arise from the claims and from combinations of two or more of these claims.

The invention is explained in greater detail below with reference to working examples, but without intending to be restricted thereby. The person skilled in the art will be able to glean from the examples working details that are not given in detail in the general description, generalise them in accordance with general expert knowledge and apply them to a specific problem.

Besides the usual and well-known abbreviations, the following abbreviations are used:

C: crystalline phase; N: nematic phase; Sm: smectic phase; I: isotropic phase. The numbers between these symbols show the transition temperatures of the substance concerned.

Temperature data are in ° C., unless indicated otherwise.

Physical, physicochemical or electro-optical parameters are determined by generally known methods, as described, inter alia, in the brochure "Merck Liquid Crystals—Licristal®—Physical Properties of Liquid Crystals—Description of the Measurement Methods", 1998, Merck KGaA, Darmstadt.

Above and below, $\Delta n$ denotes the optical anisotropy (589 nm, 20° C.) and $\Delta\varepsilon$ denotes the dielectric anisotropy (1 kHz, 20° C.). The dielectric anisotropy $\Delta\varepsilon$ is determined at 20° C. and 1 kHz. The optical anisotropy $\Delta n$ is determined at 20° C. and a wavelength of 589.3 nm.

The $\Delta\varepsilon$ and $\Delta n$ values the extrapolated clearing point (cl. p.) and the rotational viscosity ($\gamma_1$) of the compounds according to the invention are obtained by linear extrapolation from liquid-crystalline mixtures consisting of 5 to 10% of the respective compound according to the invention and 90-95% of the commercially available liquid-crystal mixture ZLI-2857 (for $\Delta\varepsilon$, cl. p.) or ZLI-4792 (for $\Delta n$, $\gamma_1$) (mixtures, Merck KGaA, Darmstadt).

The abbreviations have the following meanings below:
MTBE methyl tert-butyl ether
THF tetrahydrofuran
DMF dimethylformamide
DMAP 4-(dimethylamino)pyridine
sat. soln. saturated solution
n-BuLi, BuLi n-butyllithium, solution in hexane
RT room temperature, about 20° C.
m.p. melting point

EXAMPLES

The starting substances can be obtained in accordance with generally accessible literature procedures or commercially.

Example 1

3-Ethoxy-4,6-difluoro-7-pentyldibenzothiophene

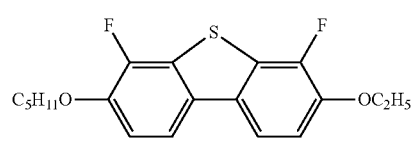

Step 1

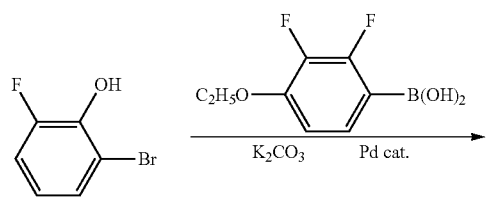

0.058 mol of 2-bromo-6-fluorophenol is dissolved in 100 ml of THF, and 40 ml of water and 0.09 mol of potassium carbonate are added. After warming to the boiling point, 0.3 mmol of tris(dibenzylideneacetone)dipalladium(0) and 0.9 mmol of cataCXium® A (di(1-adamantyl)-n-butylphosphine) are added, and a solution of 0.062 mol of (4-ethoxy-2,3-difluorophenyl)dimethoxyborane, dissolved in 100 ml of THF, is added dropwise over the course of half an hour. The mixture is boiled under reflux for a further 16 hours, water and MTB are then added, and the mixture is subjected to extractive work-up. The crude product 4'-ethoxy-3,2',3'-trifluorobiphenyl-2-ol is purified by chromatography (eluent: chlorobutane), giving white crystals.

Step 2

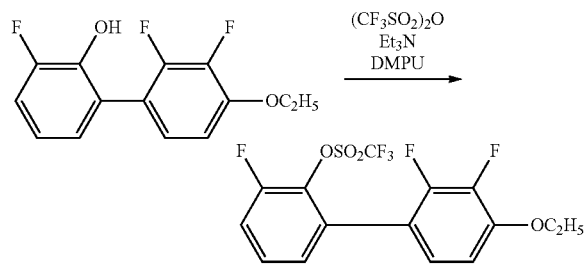

0.022 mol of 4'-ethoxy-3,2',3'-trifluorobiphenyl-2-ol, 0.036 mol of triethylamine and 0.6 mmol of DMAP are dissolved in 50 ml of dichloromethane. 0.03 mol of trifluoromethanesulfonic anhydride is added dropwise to this solution at 5-10° C. over the course of half an hour. The mixture is stirred for a further hour without further cooling, and the batch is filtered through a silica-gel column with dichloromethane. Evaporation of the filtrate gives the trifluoromethylsulfonate of 4'-ethoxy-3,2',3'-trifluorobiphenyl-2-ol.

Step 3

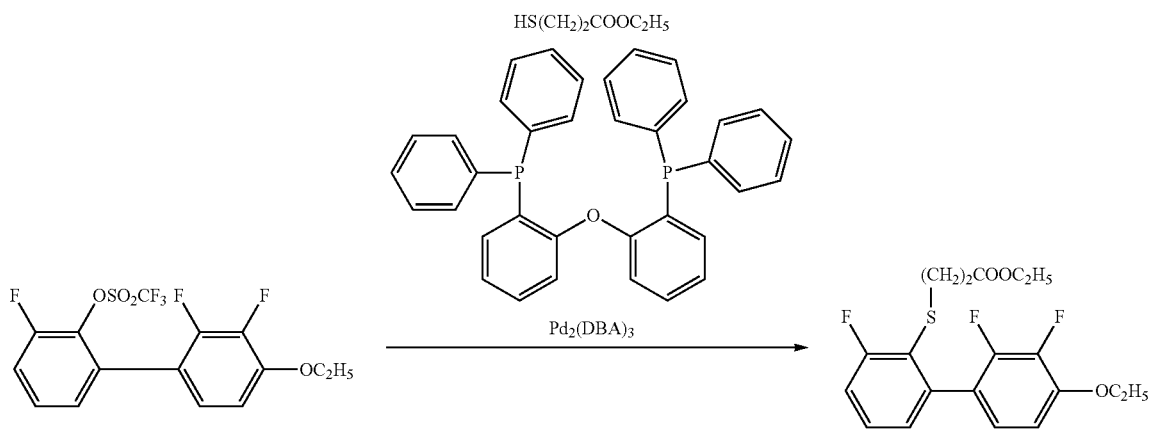

0.022 mol of the trifluoromethanesulfonate of 4'-ethoxy-3,2',3'-trifluorobiphenyl-2-ol and 0.024 mol of ethyl mercaptopropionate are dissolved in 50 ml of dry toluene and boiled under reflux for 24 hours with 2.2 mmol of bis(2-diphenylphosphinophenyl) ether, 1.1 mmol of tris(dibenzylideneacetone)dipalladium(0) and 0.055 mol of potassium carbonate. Water and MTB are added to the reaction mixture, which is then subjected to extractive work-up. The organic phase is evaporated, and the product is isolated by column chromatography on silica gel with 1-chlorobutane, giving 0.014 mol of ethyl 3-(4'-ethoxy-3,2',3'-trifluorobiphenyl-2-ylsulfanyl)propionate.

Step 4

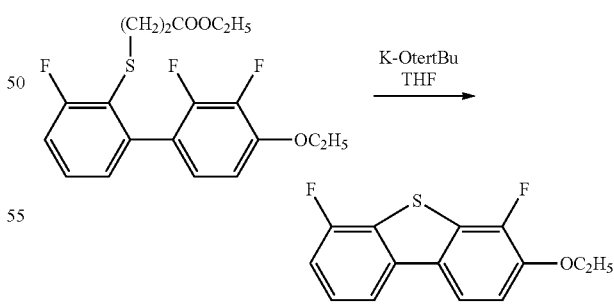

0.014 mol of ethyl 3-(4'-ethoxy-3,2',3'-trifluorobiphenyl-2-ylsulfanyl)propionate is boiled under reflux for 14 hours with 0.017 mol of potassium tert-butoxide in 50 ml of THF. Water and MTB are added to the reaction mixture, which is then subjected to extractive work-up. The organic phase is evaporated, and the product is isolated by column chromatography on silica gel with 1-chlorobutane, giving 3-ethoxy-4,6-difluorodibenzothiophene.

Step 5

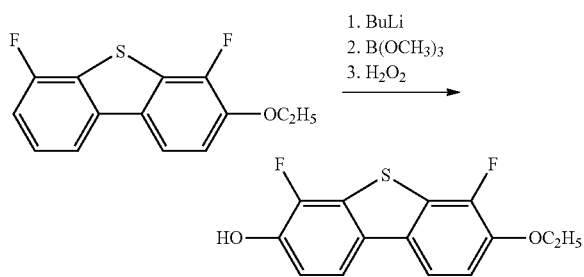

0.013 mol of 3-ethoxy-4,6-difluorodibenzothiophene is dissolved in 50 ml of THF, and 11 ml (0.017 mol) of n-BuLi (1.6 M in hexane) are added dropwise at −70° C. The mixture is stirred at −70° C. for a further 30 minutes, and 0.017 mol of trimethyl borate (dissolved in a little THF) is then added at the same temperature. The reaction mixture is warmed to room temperature, and a mixture of 2 ml of acetic acid and 2.5 ml of water is then added. 3 ml of 30% hydrogen peroxide are then added dropwise at max. 45° C. After stirring for a further 14 hours, water and MTB are added to the reaction mixture, which is then subjected to extractive work-up. The organic phase is evaporated, and the product is isolated by column chromatography on silica gel with dichloromethane, giving 0.011 mol of 7-ethoxy-4,6-difluorodibenzothiophen-3-ol.

Step 6

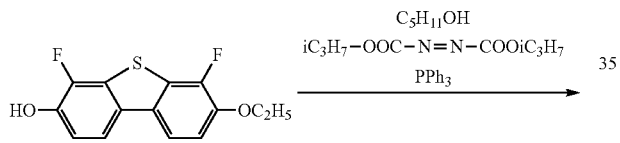

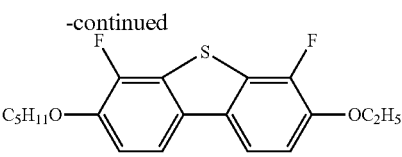

0.011 mol of 3-ethoxy-4,6-difluorodibenzothiophen-3-ol, 0.018 mol of pentan-1-ol and 0.017 mol of triphenylphosphine are dissolved in 50 ml of THF, and 0.017 mol of diisopropyl azodicarboxylate is added dropwise at room temperature. The reaction mixture is stirred for a further 14 hours, water and MTB are then added, and the mixture is subjected to extractive work-up. The organic phase is evaporated, and the product is isolated by column chromatography on silica gel with 1-chlorobutane, giving 3.6 g (0.01 mol) of 3-ethoxy-4,6-difluoro-7-pentyloxydibenzothiophene.

Melting point: 77° C.

Phases: C 77 I (cf. also table).

The following compounds are prepared analogously to Example 1:

The radicals $R^{1/2}$ are straight-chain, i.e. unbranched, unless indicated otherwise. The substance data are given in Table 1.

TABLE 1

| $R^1$ | $R^2$ | M.p. [° C.] | Δε | Δn | $\gamma_1$ [mPa · s] | Cl.p. [° C.] |
|---|---|---|---|---|---|---|
| —CH₃ | —CH₃ | | | | | |
| —CH₃ | —C₂H₅ | | | | | |
| —CH₃ | —C₃H₇ | | | | | |
| —CH₃ | —C₄H₉ | | | | | |
| —CH₃ | —C₅H₁₁ | | | | | |
| —CH₃ | —C₆H₁₃ | | | | | |
| —C₂H₅ | —C₂H₅ | 126 | | | | |
| —C₂H₅ | —C₃H₇ | 100 | −14 | 0.214 | 168 | 136 |
| —C₂H₅ | —C₄H₉ | 79 | −14 | 0.213 | 164 | 127 |
| —C₂H₅ | —CH₂CH(CH₃)₂ | | | | | |
| —C₂H₅ | —CH₂CH(CH₃)₂ | | | | | |
| —C₂H₅ | —(CH₂)₂CH=CH₂ | | | | | |
| —C₂H₅ | —(CH₂)₂CH(CH₃)₂ | | | | | |
| —C₂H₅ | —C₅H₁₁ | 77 | −13 | 0.196 | 197 | 120 |
| —C₂H₅ | —C₆H₁₃ | 77 | −13 | 0.197 | 183 | 121 |
| —C₂H₅ | —C₇H₁₅ | 86 | −12 | 0.187 | 222 | 114 |
| —C₂H₅ | —(CH₂)₃CH(CH₃)₂ | | | | | |
| —C₃H₇ | —C₃H₇ | 97 | −14 | 0.206 | 189 | 120 |
| —C₃H₇ | —C₄H₉ | 85 | −13 | 0.199 | 186 | 118 |
| —C₃H₇ | —C₅H₁₁ | 80 | −13 | 0.189 | 179 | 111 |
| —C₃H₇ | —C₆H₁₃ | 80 | −13 | 0.191 | 210 | 113 |
| —C₃H₇ | —C₇H₁₅ | 77 | −12 | 0.181 | 226 | 108 |
| —C₄H₉ | —C₄H₉ | 85 | −13 | 0.194 | 195 | 115 |
| —C₄H₉ | —C₅H₁₁ | 84 | −12 | 0.186 | 176 | 112 |
| —C₄H₉ | —(CH₂)₂CH=CHCH₃[*] | | | | | |
| —C₄H₉ | —C₆H₁₃ | 74 | −12 | 0.182 | 202 | 112 |
| —C₄H₉ | —C₇H₁₅ | 68 | −12 | 0.177 | 204 | 109 |

TABLE 1-continued

| R¹ | R² | M.p. [° C.] | Δε | Δn | γ₁ [mPa · s] | Cl.p. [° C.] |
|---|---|---|---|---|---|---|
| —C₅H₁₁ | —C₅H₁₁ | 85 | −14 | 0.163 | 142 | 100 |
| —C₅H₁₁ | —C₆H₁₃ | | | | | |
| —C₆H₁₃ | —C₆H₁₃ | 85 | −12 | 0.166 | 183 | 106 |

*⁾trans isomer

The following compounds are prepared analogously to Example 1 and Scheme 2:

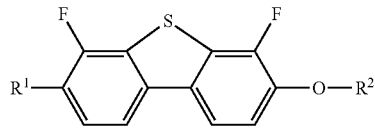

The radicals $R^{1/2}$ are straight-chain, i.e. unbranched, unless indicated otherwise. The substance data are given in Table 2.

The following compounds are prepared analogously to Example 1 and Scheme 3:

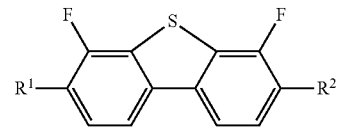

The radicals $R^{1/2}$ are straight-chain, i.e. unbranched, unless indicated otherwise. The substance data are given in Table 3.

TABLE 2

| R¹ | R² | M.p. [° C.] | Δε | Δn | γ₁ [mPa · s] | Cl.p. [° C.] |
|---|---|---|---|---|---|---|
| —CH₃ | —CH₃ | | | | | |
| —CH₃ | —C₂H₅ | 105 | −9.8 | 0.219 | 130 | 100 |
| —CH₃ | —C₃H₇ | 105 | −9.8 | 0.205 | 111 | 97 |
| —CH₃ | —C₄H₉ | 87 | −8.9 | 0.195 | 107 | 101 |
| —CH₃ | —C₅H₁₁ | 73 | −9.0 | 0.195 | 110 | 81 |
| —CH₃ | —C₆H₁₃ | | | | | |
| —C₂H₅ | —CH₃ | | | | | |
| —C₂H₅ | —C₂H₅ | 101 | −9.2 | 0.203 | 123 | 75 |
| —C₂H₅ | —C₃H₇ | 70 | −8.6 | 0.188 | 118 | 68 |
| —C₂H₅ | —C₄H₉ | 69 | −8.7 | 0.187 | 116 | 69 |
| —C₂H₅ | —CH₂CH(CH₃)₂ | | | | | |
| —C₂H₅ | —(CH₂)₂CH=CH₂ | | | | | |
| —C₂H₅ | —(CH₂)₂CH(CH₃)₂ | | | | | |
| —C₂H₅ | —C₅H₁₁ | | | | | |
| —C₂H₅ | —C₆H₁₃ | | | | | |
| —C₂H₅ | —(CH₂)₃CH(CH₃)₂ | | | | | |
| —C₃H₇ | —CH₃ | | | | | |
| —C₃H₇ | —C₂H₅ | 105 | −9.6 | 0.201 | 147 | 78 |
| —C₃H₇ | —C₃H₇ | 73 | −8.7 | 0.188 | 139 | 74 |
| —C₃H₇ | —C₄H₉ | 72 | −8.7 | 0.184 | 133 | 75 |
| —C₃H₇ | —(CH₂)₂CH=CH₂ | | | | | |
| —C₃H₇ | —C₅H₁₁ | | | | | |
| —C₃H₇ | —C₆H₁₃ | | | | | |
| —C₄H₉ | —CH₃ | | | | | |
| —C₄H₉ | —C₂H₅ | 80 | −9.2 | 0.191 | 137 | 73 |
| —C₄H₉ | —C₃H₇ | 62 | −8.9 | 0.180 | 135 | 67 |
| —(CH₂)₂—CH=CH₂ | —C₂H₅ | | | | | |
| —C₄H₉ | —C₄H₉ | 62 | −8.6 | 0.177 | 123 | 64 |
| —C₄H₉ | —C₅H₁₁ | | | | | |
| —C₄H₉ | —(CH₂)₂CH=CHCH₃*⁾ | | | | | |
| —C₄H₉ | —C₆H₁₃ | | | | | |
| —C₅H₁₁ | —CH₃ | | | | | |
| —C₅H₁₁ | —C₂H₅ | 71 | −8.9 | 0.191 | 158 | 80 |
| —(CH₂)₂—CH=CH—CH₃*⁾ | —C₂H₅ | | | | | |
| —C₅H₁₁ | —C₃H₇ | 71 | −7.7 | 0.181 | 143 | 72 |
| —C₅H₁₁ | —C₄H₉ | 69 | −8.6 | 0.179 | 144 | 73 |
| —C₅H₁₁ | —(CH₂)₂CH=CH₂ | | | | | |
| —C5H₁₁ | —C₆H₁₃ | | | | | |

*⁾trans isomer

TABLE 3

| R¹ | R² | M.p. [° C.] | Δε | Δn | γ₁ [mPa · s] | Cl.p. [° C.] |
|---|---|---|---|---|---|---|
| —CH₃ | —CH₃ | | | | | |
| —CH₃ | —C₂H₅ | | | | | |
| —CH₃ | —C₃H₇ | | | | | |
| —CH₃ | —C₄H₉ | | | | | |
| —CH₃ | —C₅H₁₁ | 50 | −5.6 | 0.170 | 86 | 42 |
| —CH₃ | —C₆H₁₃ | | | | | |
| —CH₃ | —(CH₂)₂CH=CH₂ | 42 | −6.2 | 0.185 | 76 | 48 |
| —CH₃ | —(CH₂)₂CH=CHCH₃*⁾ | | | | | |
| —C₂H₅ | —C₂H₅ | | | | | |
| —C₂H₅ | —C₃H₇ | 66 | −7.2 | 0.166 | 71 | 15 |
| —C₂H₅ | —C₄H₉ | | | | | |
| —C₂H₅ | —CH₂CH(CH₃)₂ | | | | | |
| —C₂H₅ | —(CH₂)₂CH=CH₂ | | | | | |
| —C₂H₅ | —(CH₂)₂CH(CH₃)₂ | | | | | |
| —C₂H₅ | —C₅H₁₁ | | | | | |
| —C₂H₅ | —C₆H₁₃ | | | | | |
| —C₂H₅ | —(CH₂)₃CH(CH₃)₂ | | | | | |
| —C₃H₇ | —C₃H₇ | | | | | |
| —C₃H₇ | —C₄H₉ | 57 | −4.9 | 0.154 | 80 | 14 |
| —C₃H₇ | —(CH₂)₂CH=CH₂ | | | | | |
| —C₃H₇ | —C₅H₁₁ | | | | | |
| —C₃H₇ | —C₆H₁₃ | | | | | |
| —C₄H₉ | —C₄H₉ | | | | | |
| —(CH₂)₂—CH=CH₂ | —(CH₂)₂CH=CH₂ | 75 | −6.6 | 0.184 | 61 | 32 |
| —C₄H₉ | —C₅H₁₁ | | | | | |
| —C₄H₉ | —(CH₂)₂CH=CHCH₃*⁾ | | | | | |
| —C₄H₉ | —C₆H₁₃ | | | | | |
| —C₅H₁₁ | —(CH₂)₂CH=CH₂ | | | | | |
| —C₅H₁₁ | —C₆H₁₃ | | | | | |

*⁾trans isomer

The following compounds are prepared analogously to Example 1:

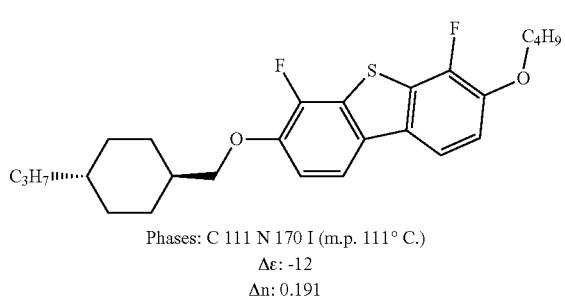

Phases: C 111 N 170 I (m.p. 111° C.)
Δε: −12
Δn: 0.191
γ₁ [mPa·s]: 954

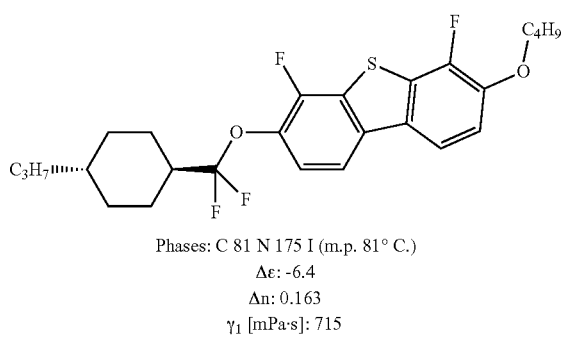

Phases: C 81 N 175 I (m.p. 81° C.)
Δε: −6.4
Δn: 0.163
γ₁ [mPa·s]: 715

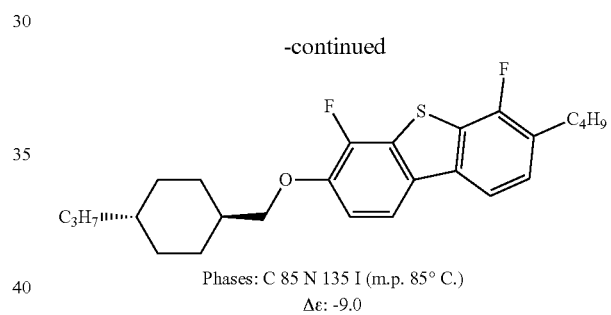

Phases: C 85 N 135 I (m.p. 85° C.)
Δε: −9.0
Δn: 0.173
γ₁ [mPa·s]: 769

Phases: C 99 N 212 I (m.p. 99° C.)
Δε: −9.4
Δn: 0.201
γ₁ [mPa·s]: 1019

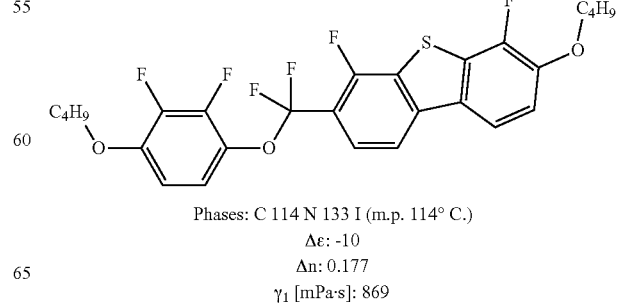

Phases: C 114 N 133 I (m.p. 114° C.)
Δε: −10
Δn: 0.177
γ₁ [mPa·s]: 869

-continued

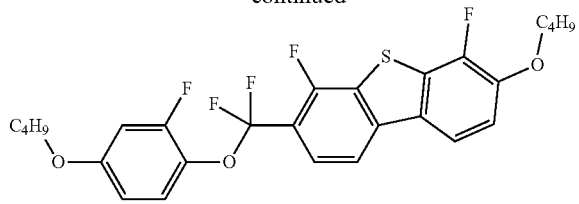

Phases: C 74 N 132 I (m.p. 74° C.)
Δε: -7.2
Δn: 0.190
γ₁ [mPa·s]: 1086

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

The entire disclosure[s] of all applications, patents and publications, cited herein and of corresponding DE application No. 10 2014 005 713.5, filed Apr. 22, 2014 are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

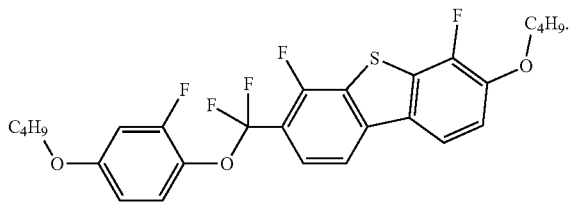

IB-1

IB-2
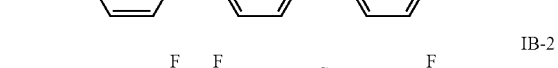

IB-3

IB-4

IB-5
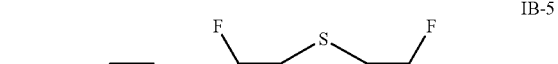

IB-6
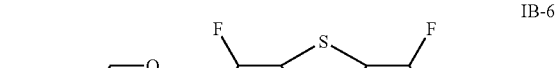

IB-7
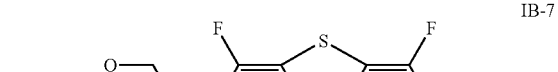

IC-1
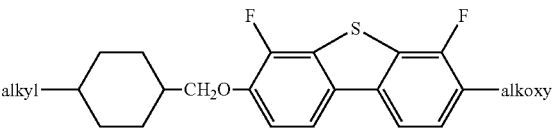

IC-2
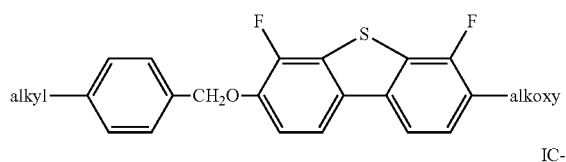
IC-3
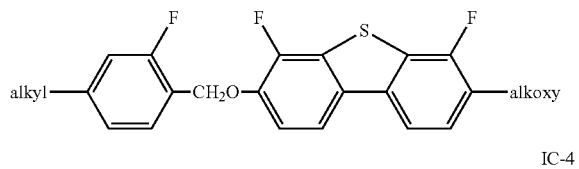
IC-4
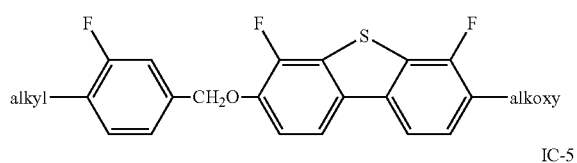
IC-5
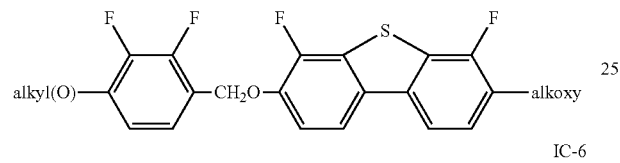
IC-6
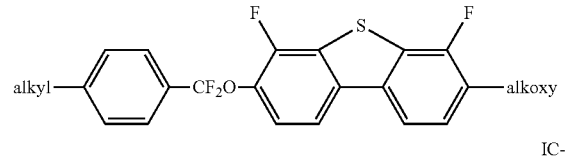
IC-7
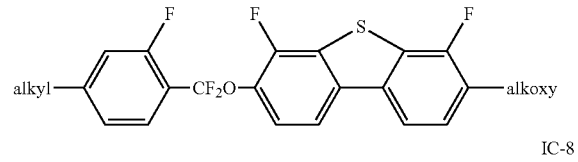
IC-8
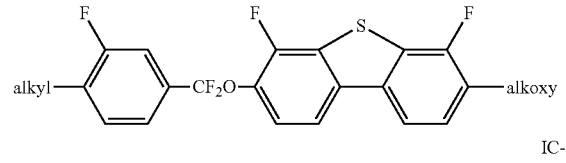
IC-9
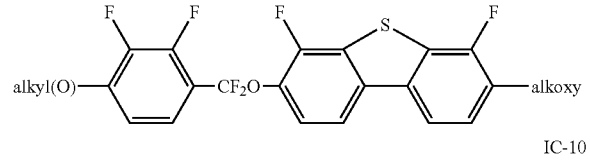
IC-10
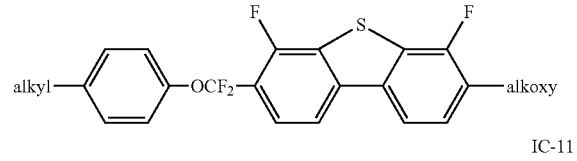
IC-11
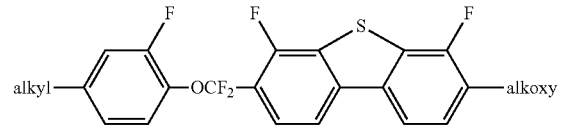
IC-12
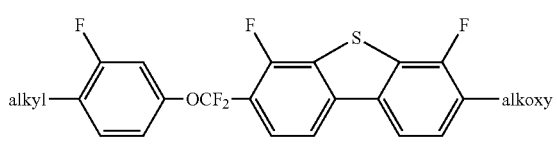
IC-13
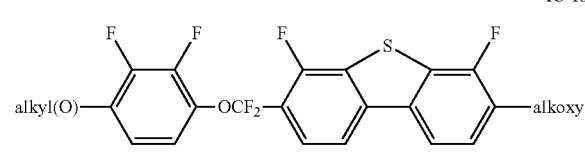
in which alkyl, independently of one another, denotes a straight-chain alkyl radical having 1-7 C atoms, and alkyl(O) stands for alkyl or alkoxy having 1 to 7 C atoms.
19. A compound according to claim 1, which is one of the following compounds
IA-1-1
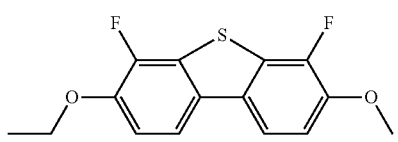
IA-1-2
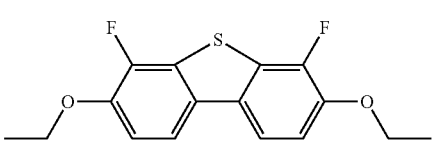
IA-1-4
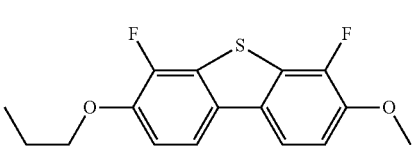
IA-1-5
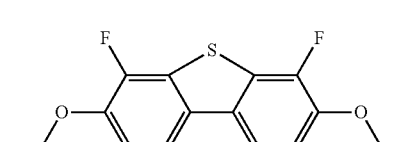
IA-1-6
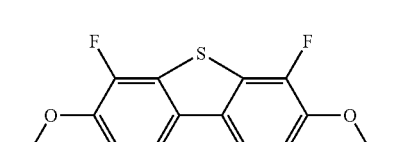
IA-1-7
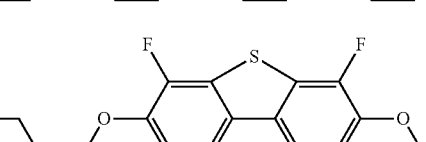
IA-1-8
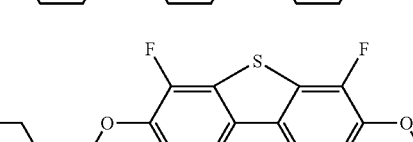

-continued
IA-1-9
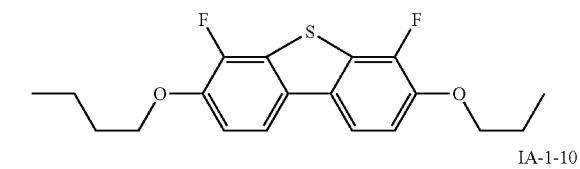
IA-1-10
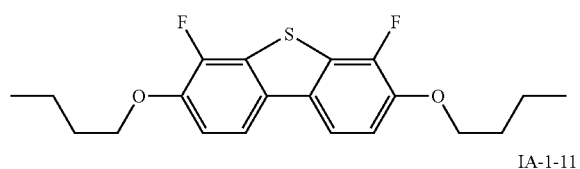
IA-1-11
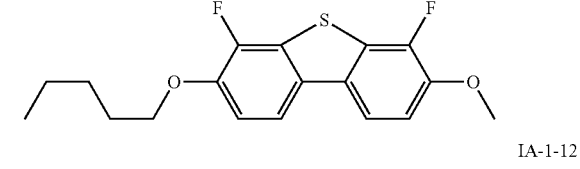
IA-1-12
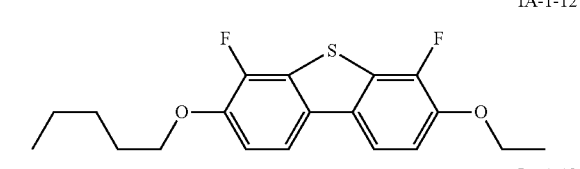
IA-1-13
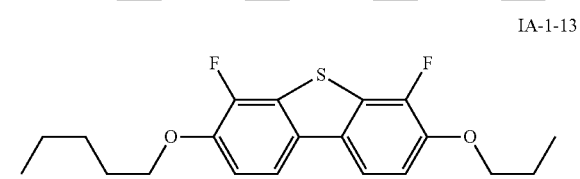
IA-1-14
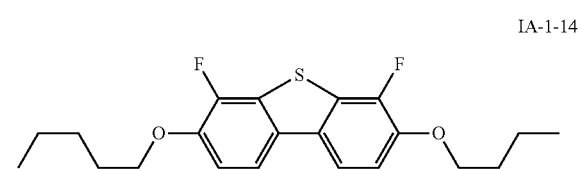
IA-1-15
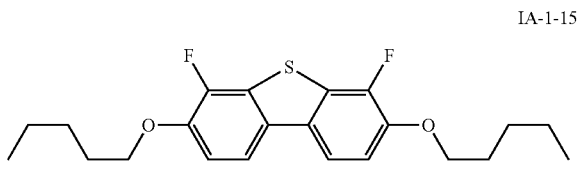
IA-1-16
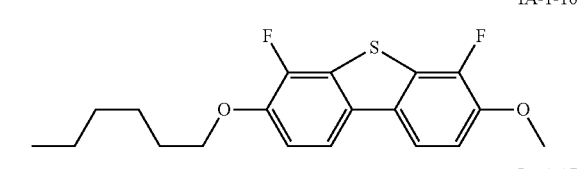
IA-1-17
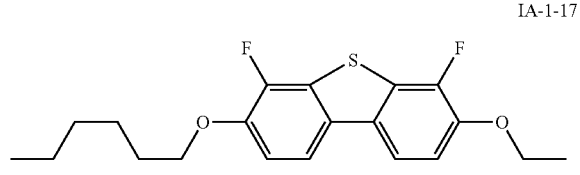
IA-1-18
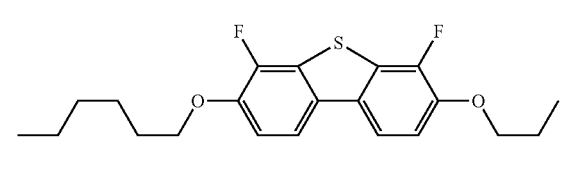
-continued
IA-1-19
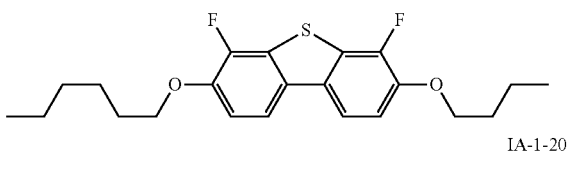
IA-1-20
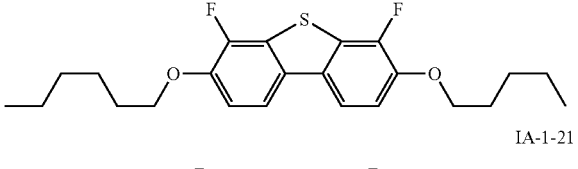
IA-1-21
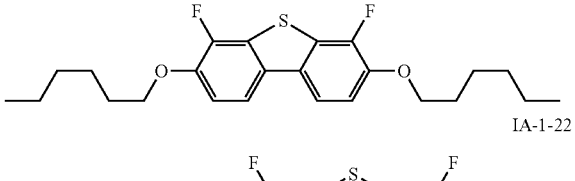
IA-1-22
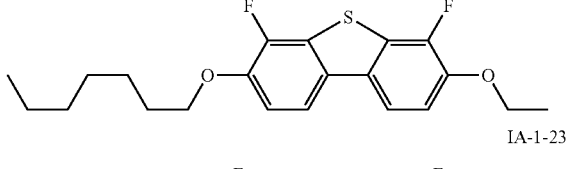
IA-1-23
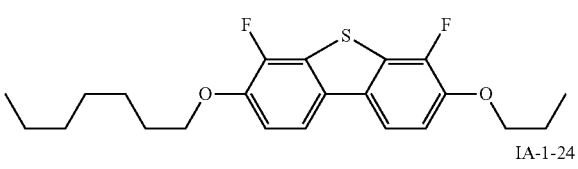
IA-1-24
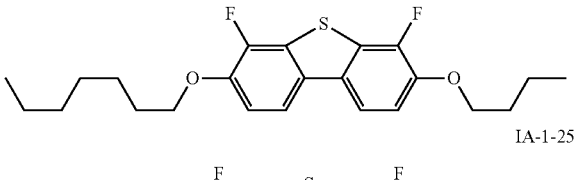
IA-1-25
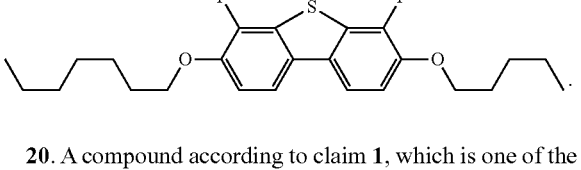
20. A compound according to claim 1, which is one of the following compounds
IA-2-1
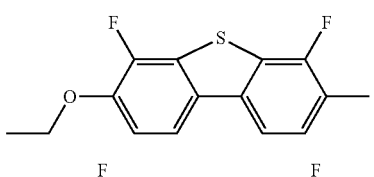
IA-2-2
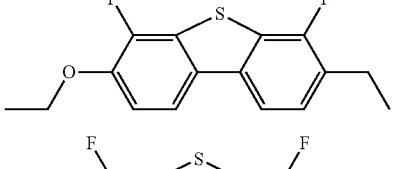
IA-2-3
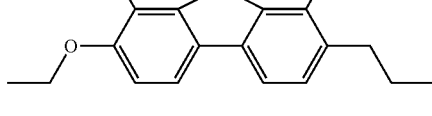

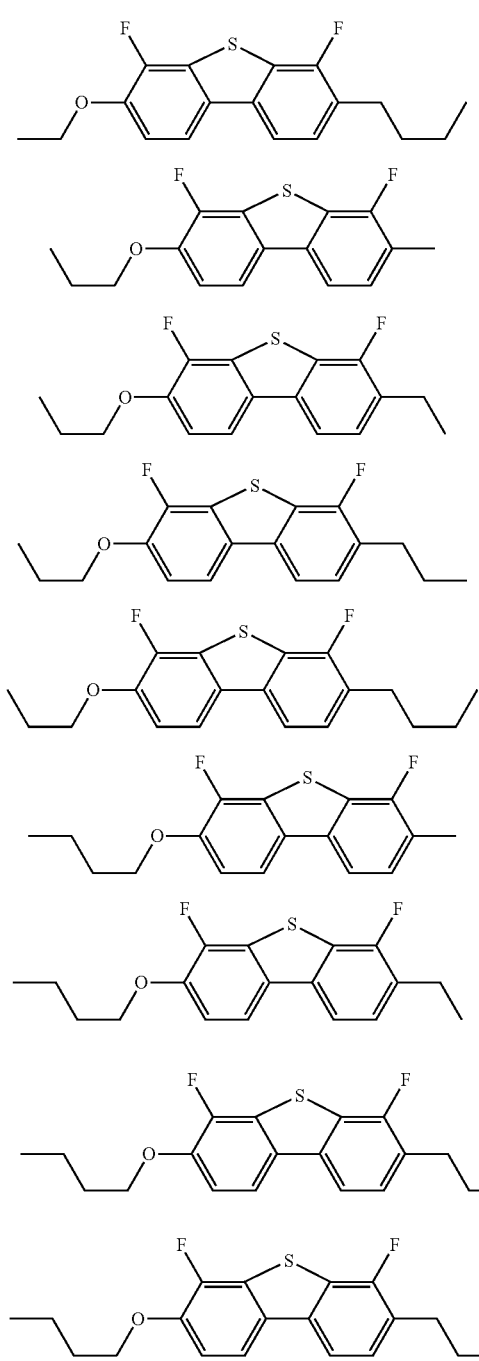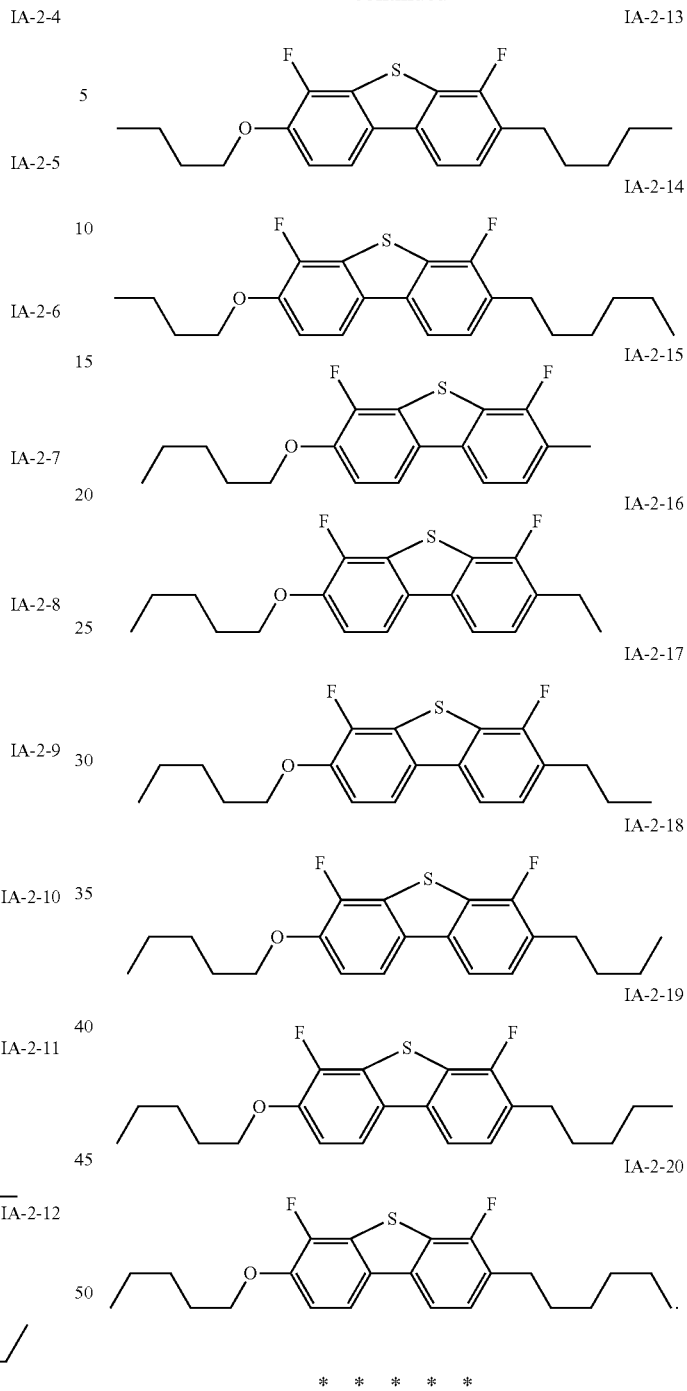

The invention claimed is:

1. A compound of formula I:

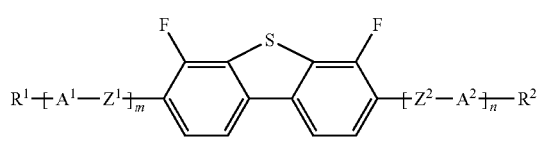

in which
m and n, independently of one another, are each 0, 1 or 2,
R¹ and R², independently of one another, denote an alkyl or alkoxy radical having 1 to 15 C atoms, in which one or more CH₂ groups are optionally replaced, independently of one another, by —C≡C—, —CF₂O—, —OCF₂—, —CH=CH—,

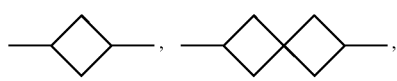

—O—, —CO—O— or —O—CO— in such a way that O atoms are not linked directly to one another, and in which one or more H atoms are optionally replaced by halogen,
A¹ and A², independently of one another, denote
a) 1,4-phenylene, in which one or two CH groups are optionally replaced by N and in which one or more H atoms are optionally replaced by L,
b) trans-1,4-cyclohexylene or 1,4-cyclohexenylene, in which one or more non-adjacent CH₂ groups are optionally replaced by —O— and/or —S— and in which one or more H atoms are optionally replaced by F or Cl, or
c) tetrahydropyran-2,5-diyl, 1,3-dioxane-2,5-diyl, tetrahydrofuran-2,5-diyl, cyclobutane-1,3-diyl, piperidine-1,4-diyl, thiophene-2,5-diyl or selenophene-2,5-diyl, each of which is optionally mono- or polysubstituted by L,
L on each occurrence, independently, denotes F, Cl, CN, SCN, SF₅ or straight-chain or branched, in each case optionally fluorinated, alkyl, alkoxy, alkylcarbonyl, alkoxycarbonyl, alkylcarbonyloxy or alkoxycarbonyloxy having 1 to 12 C atoms, and
Z¹ and Z², independently of one another, denote a single bond, —CF₂O—, —OCF₂—, —CH₂O—, —OCH₂—, —(CO)O—, —O(CO)—, —(CH₂)₄—, —CH₂CH₂—, —CF₂—CF₂—, —CF₂—CH₂—, —CH₂—CF₂—, —CH=CH—, —CF=CF—, —CF=CH—, —CH=CF—, —(CH₂)₃O—, —O(CH₂)₃—, —C≡C—, —O—, —CH₂—, —(CH₂)₃— or —CF₂.

2. A compound according to claim 1, wherein the sum m+n is 0 or 1.

3. A compound according to claim 1, wherein
R¹ and R², independently of one another, denote an unsubstituted alkyl radical or alkoxy radical having 1 to 15 carbon atoms or an alkenyl, alkenyloxy or alkynyl radical having 2 to 15 C atoms, which are in each case optionally mono- or polyhalogenated.

4. A compound according claim 1, wherein m+n=0.

5. A compound according to claim 1, which is one of formula IA to IC

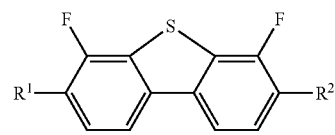

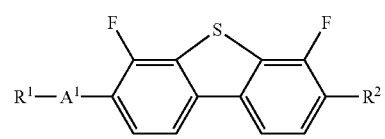

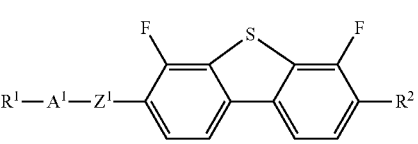

in which
R¹, R², A¹ and Z¹ have the meanings as for the compound of formula I.

6. A compound according to claim 1, which is one of formulae IA-1 to IA-10,

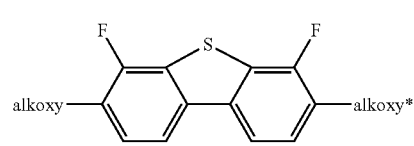

-continued

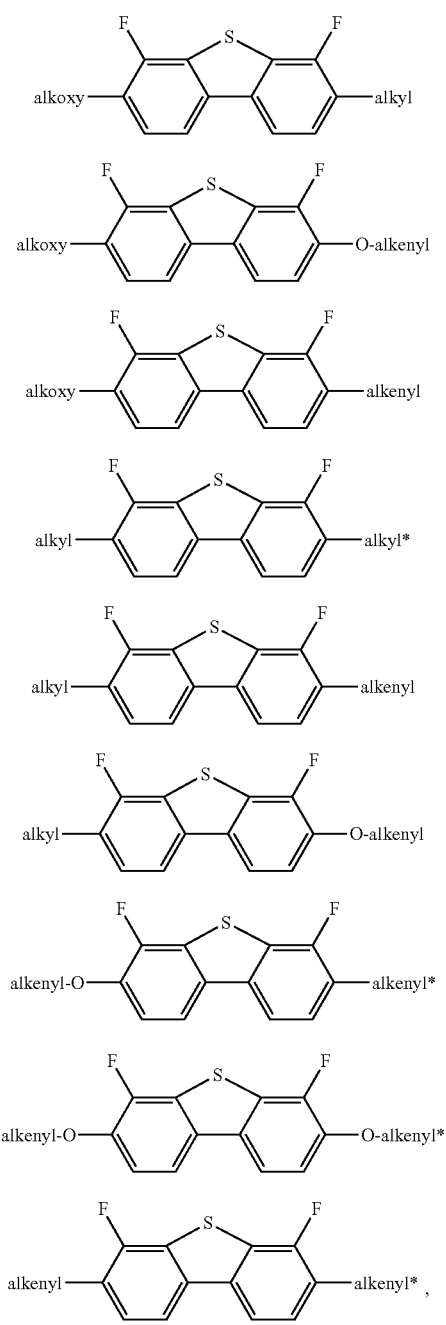

in which alkyl and alkyl* each, independently of one another, denote a straight-chain alkyl radical having 1-7 C atoms, alkenyl and alkenyl* each, independently of one another, denote a straight-chain alkenyl radical having 2-7 C atoms, alkoxy and alkoxy* each, independently of one another, denote a straight-chain alkoxy radical having 1-7 C atoms.

7. A compound according to claim 1, wherein $R^1$ and $R^2$, independently of one another, denote an alkoxy or alkyl radical having 1 to 7 carbon atoms or an alkenyl radical having 2 to 7 carbon atoms.

8. A compound according to claim 1, wherein $R^1$ and $R^2$ each denote an alkoxy group having 1 to 7 carbon atoms.

9. A compound according to claim 1, wherein m+n=1 or 2, and the ring $A^1$ is in each case one of the following

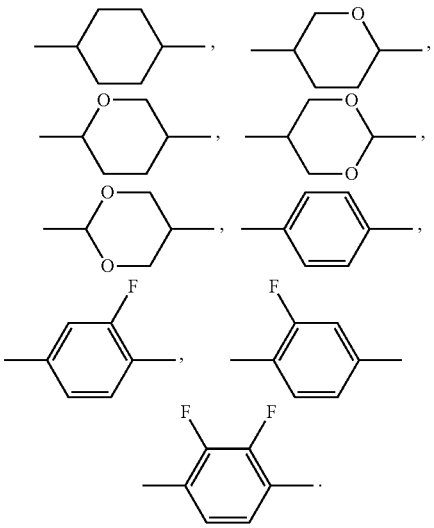

10. A liquid-crystalline medium comprising at least two compounds, one of which is a compound according to claim 1.

11. An electro-optical display element containing a liquid-crystalline medium according to claim 10.

12. A process for preparing a compound of formula I according to claim 1, comprising deprotonating a compound of formula (B) at position 3

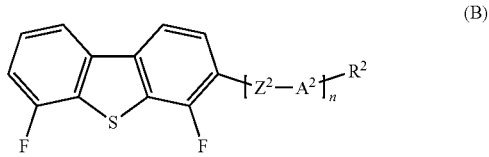

in which $Z^2$, $A^2$, n and $R^2$, independently, are defined as in the compound of formula I,
by a deprotonating reagent and converting into a compound of formula (C)

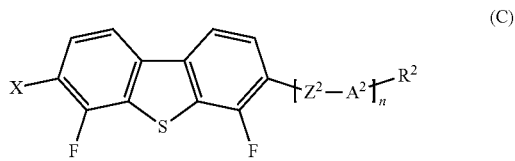

in which, independently,
X denotes $B(OR)_2$, —$C(OH)R_2$, —(CO)OH, —(CO)Cl, OH or

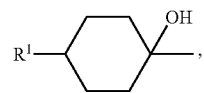

R, independently, denotes H or an alkyl radical having 1 to 14 C atoms, and $Z^2$, $A^2$, n, $R^1$ and $R^2$ are defined as in the compound of formula I, and converting into a compound of formula I.

13. A compound according to claim 1, which is

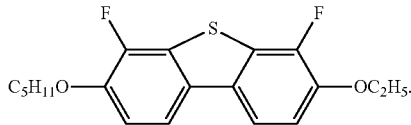

14. A compound according to claim 1, which is one of the following compounds

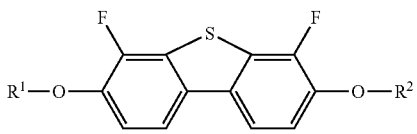

wherein $R^1$ and $R^2$ are straight-chain unless indicated otherwise

| $R^1$ | $R^2$ |
|---|---|
| —CH₃ | —CH₃ |
| —CH₃ | —C₂H₅ |
| —CH₃ | —C₃H₇ |
| —CH₃ | —C₄H₉ |
| —CH₃ | —C₅H₁₁ |
| —CH₃ | —C₆H₁₃ |
| —C₂H₅ | —C₂H₅ |
| —C₂H₅ | —C₃H₇ |
| —C₂H₅ | —C₄H₉ |
| —C₂H₅ | —(CH₂)₂CH=CH₂ |
| —C₂H₅ | —(CH₂)₂CH(CH₃)₂ |
| —C₂H₅ | —C₅H₁₁ |
| —C₂H₅ | —C₆H₁₃ |
| —C₂H₅ | —C₇H₁₅ |
| —C₂H₅ | —(CH₂)₃CH(CH₃)₂ |
| —C₃H₇ | —C₃H₇ |
| —C₃H₇ | —C₄H₉ |
| —C₃H₇ | —C₅H₁₁ |
| —C₃H₇ | —C₆H₁₃ |
| —C₃H₇ | —C₇H₁₅ |
| —C₄H₉ | —C₄H₉ |
| —C₄H₉ | —C₅H₁₁ |
| —C₄H₉ | —(CH₂)₂CH=CHCH₃*) |
| —C₄H₉ | —C₆H₁₃ |
| —C₄H₉ | —C₇H₁₅ |
| —C₅H₁₁ | —C₅H₁₁ |
| —C₅H₁₁ | —C₆H₁₃ |
| —C₆H₁₃ | —C₆H₁₃ | wherein *) means trans isomer.

15. A compound according to claim 1, which is one of the following compounds

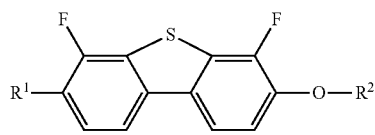

wherein $R^1$ and $R^2$ are straight-chain unless indicated otherwise

| $R^1$ | $R^2$ |
|---|---|
| —CH₃ | —CH₃ |
| —CH₃ | —C₂H₅ |
| —CH₃ | —C₃H₇ |
| —CH₃ | —C₄H₉ |
| —CH₃ | —C₅H₁₁ |
| —CH₃ | —C₆H₁₃ |
| —C₂H₅ | —CH₃ |
| —C₂H₅ | —C₂H₅ |
| —C₂H₅ | —C₃H₇ |
| —C₂H₅ | —C₄H₉ |
| —C₂H₅ | —CH₂CH(CH₃)₂ |
| —C₂H₅ | —(CH₂)₂CH=CH₂ |
| —C₂H₅ | —(CH₂)₂CH(CH₃)₂ |
| —C₂H₅ | —C₅H₁₁ |
| —C₂H₅ | —C₆H₁₃ |
| —C₂H₅ | —(CH₂)₃CH(CH₃)₂ |
| —C₃H₇ | —CH₃ |
| —C₃H₇ | —C₂H₅ |
| —C₃H₇ | —C₃H₇ |
| —C₃H₇ | —C₄H₉ |
| —C₃H₇ | —(CH₂)₂CH=CH₂ |
| —C₃H₇ | —C₅H₁₁ |
| —C₃H₇ | —C₆H₁₃ |
| —C₄H₉ | —CH₃ |
| —C₄H₉ | —C₂H₅ |
| —C₄H₉ | —C₃H₇ |
| —(CH₂)₂CH=CH₂ | —C₂H₅ |
| —C₄H₉ | —C₄H₉ |
| —C₄H₉ | —C₅H₁₁ |
| —C₄H₉ | —(CH₂)₂CH=CHCH₃*) |
| —C₄H₉ | —C₆H₁₃ |
| —C₅H₁₁ | —CH₃ |
| —C₅H₁₁ | —C₂H₅ |
| —(CH₂)₂CH=CHCH₃*) | —C₂H₅ |
| —C₅H₁₁ | —C₃H₇ |
| —C₅H₁₁ | —C₄H₉ |
| —C₅H₁₁ | —(CH₂)₂CH=CH₂ |
| —C₅H₁₁ | —C₆H₁₃ | wherein *) means trans isomer.

16. A compound according to claim 1, which is one of the following compounds

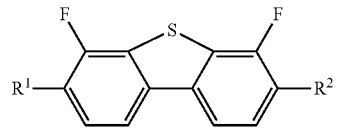

wherein $R^1$ and $R^2$ are straight-chain unless indicated otherwise

| $R^1$ | $R^2$ |
|---|---|
| —CH₃ | —CH₃ |
| —CH₃ | —C₂H₅ |
| —CH₃ | —C₃H₇ |
| —CH₃ | —C₄H₉ |
| —CH₃ | —C₅H₁₁ |
| —CH₃ | —C₆H₁₃ |
| —CH₃ | —(CH₂)₂CH=CH₂ |
| —CH₃ | —(CH₂)₂CH=CHCH₃*) |
| —C₂H₅ | —C₂H₅ |
| —C₂H₅ | —C₃H₇ |
| —C₂H₅ | —C₄H₉ |
| —C₂H₅ | —CH₂CH(CH₃)₂ |
| —C₂H₅ | —(CH₂)₂CH=CH₂ |
| —C₂H₅ | —(CH₂)₂CH(CH₃)₂ |
| —C₂H₅ | —C₅H₁₁ |

-continued

| $R^1$ | $R^2$ |
|---|---|
| —$C_2H_5$ | —$C_6H_{13}$ |
| —$C_2H_5$ | —$(CH_2)_3CH(CH_3)_2$ |
| —$C_3H_7$ | —$C_3H_7$ |
| —$C_3H_7$ | —$C_4H_9$ |
| —$C_3H_7$ | —$(CH_2)_2CH=CH_2$ |
| —$C_3H_7$ | —$C_5H_{11}$ |
| —$C_3H_7$ | —$C_6H_{13}$ |
| —$C_4H_9$ | —$C_4H_9$ |
| —$(CH_2)_2$—CH=$CH_2$ | —$(CH_2)_2CH=CH_2$ |
| —$C_4H_9$ | —$C_5H_{11}$ |
| —$C_4H_9$ | —$(CH_2)_2CH=CHCH_3$*) |
| —$C_4H_9$ | —$C_6H_{13}$ |
| —$C_5H_{11}$ | —$(CH_2)_2CH=CH_2$ |
| —$C_5H_{11}$ | —$C_6H_{13}$ | wherein *) means trans isomer.

17. A compound according to claim 1, which is one of the following compounds

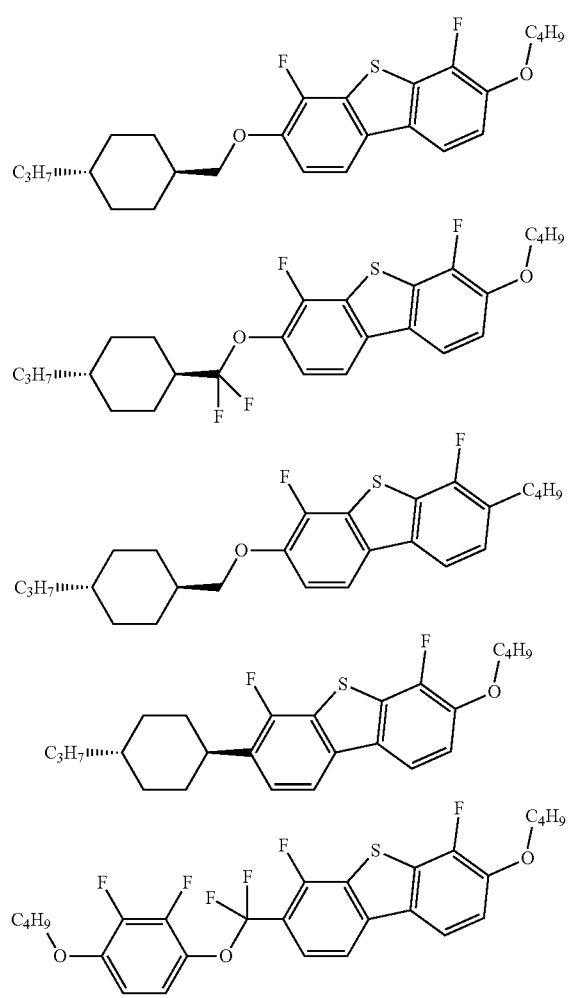

18. A compound according to claim 1, which is one of formulae IB-1 to IC-13,